US012773182B2

(12) United States Patent
Scott

(10) Patent No.: US 12,773,182 B2
(45) Date of Patent: Oct. 27, 2026

(54) METHOD OF DETECTION OF MICROCALCIFICATIONS BY ULTRASOUND

(71) Applicant: UltraVision Corporation, Palm Beach Gardens, FL (US)

(72) Inventor: William Charles Scott, North Palm Beach, FL (US)

(73) Assignee: Ultravision Corporation, Palm Beach Gardens, FL (US)

( * ) Notice: Subject to any disclaimer, the term of this patent is extended or adjusted under 35 U.S.C. 154(b) by 107 days.

(21) Appl. No.: 17/821,381

(22) Filed: Aug. 22, 2022

(65) Prior Publication Data

US 2023/0181154 A1 Jun. 15, 2023

Related U.S. Application Data

(63) Continuation-in-part of application No. 16/749,728, filed on Jan. 22, 2020, now abandoned.

(60) Provisional application No. 62/795,419, filed on Jan. 22, 2019.

(51) Int. Cl.
*A61B 8/08* (2006.01)
*A61B 8/00* (2006.01)

(52) U.S. Cl.
CPC ............ *A61B 8/085* (2013.01); *A61B 8/5207* (2013.01)

(58) Field of Classification Search
CPC ........... A61B 8/08; A61B 8/085; A61B 8/485; A61B 8/5207; A61B 8/5223
See application file for complete search history.

(56) References Cited

U.S. PATENT DOCUMENTS

| | | | | |
|---|---|---|---|---|
| 6,589,177 | B1 * | 7/2003 | Detmer | G01S 7/52066 600/443 |
| 9,585,636 | B2 * | 3/2017 | Osumi | G06T 5/70 |
| 2001/0044580 | A1 | 11/2001 | Pellegretti et al. | |
| 2005/0154306 | A1 * | 7/2005 | Burcher | G01S 7/52049 600/447 |
| 2009/0247869 | A1 | 10/2009 | Rambod et al. | |
| 2010/0087736 | A1 * | 4/2010 | Katsuyama | G01S 7/52071 600/443 |

(Continued)

FOREIGN PATENT DOCUMENTS

| | | |
|---|---|---|
| CN | 102014756 | 4/2011 |
| CN | 101023376 | 5/2011 |
| WO | WO2014096789 | 6/2014 |

OTHER PUBLICATIONS

Ronny X. Li, "Ultrasonic Pulse Wave Imaging for in vivo Assessment of Vascular Wall Dynamics and Characterization of Arterial Pathologies", Columbia University, 2016 (Year: 2016).*

*Primary Examiner* — Brooke Lyn Klein
(74) *Attorney, Agent, or Firm* — McHale & Slavin, P.A.

(57) ABSTRACT

Methods and devices for imaging of microcalcification particles using ultrasound. The method may include delivering a multi-pulse transmit packet of an acoustic line to a predetermined location within a tissue having or suspected of having a microcalcification; causing the microcalcification to move or oscillate, comparing one or more received signals from the location over one or more transmissions, and determining frequency modulation of the returning pulses as a result of the microcalcification oscillation or random pattern movement.

6 Claims, 15 Drawing Sheets

(56) References Cited

U.S. PATENT DOCUMENTS

| | | | | |
|---|---|---|---|---|
| 2013/0018265 | A1* | 1/2013 | Kim | A61B 8/145 600/443 |
| 2013/0109972 | A1 | 5/2013 | Liu | |
| 2015/0320384 | A1* | 11/2015 | Cunitz | A61B 8/0858 600/431 |
| 2016/0296202 | A1 | 10/2016 | Robert et al. | |
| 2017/0055956 | A1* | 3/2017 | Osumi | G01S 7/52085 |
| 2018/0073353 | A1* | 3/2018 | Malik | E21B 47/0025 |
| 2018/0185010 | A1* | 7/2018 | Gu | A61B 8/481 |
| 2019/0254629 | A1* | 8/2019 | Li | G01N 29/14 |
| 2020/0138411 | A1* | 5/2020 | Olesen | A61B 8/5207 |
| 2021/0186464 | A1 | 6/2021 | Kim et al. | |

* cited by examiner

116

118

METHOD OF DETECTION OF MICROCALCIFICATIONS BY ULTRASOUND

CROSS REFERENCE

In accordance with 37 C.F.R. 1.76, a claim of priority is included in an Application Data Sheet filed concurrently herewith. Accordingly, the present invention is a continuation-in-part application of U.S. patent application Ser. No. 16,749,728, entitled, "METHOD OF DETECTION OF MICROCALCIFICATIONS BY ULTRASOUND", filed Jan. 22, 2020, which claims priority to U.S. Provisional Application No. 62/795,419, entitled, "METHOD OF DETECTION OF MICROCALCIFICATIONS BY ULTRASOUND", filed Jan. 22, 2019. The contents of the above referenced application are incorporated herein by reference in its entirety.

FIELD OF THE INVENTION

The present invention relates to devices and methods related to medical imaging and detection; to devices and methods for sound based nondestructive testing; to devices and methods related to ultrasonic medical imaging; to imaging of small particles with a large difference in acoustic impedance from the surrounding medium; and more particularly, to devices and methods for imaging of microcalcification particles using ultrasound, and to devices and methods for imaging of microcalcification particles using ultrasound as indicators of cancer.

BACKGROUND OF THE INVENTION

Diagnostic Medical Ultrasound is the most ubiquitous method of imaging because it does no harm, causes no pain, produces high resolution images, and is the lowest cost medical imaging method. It functions by emitting a pulse of ultrasonic energy in a specific location and direction into the patient and recording the amplitude and time of return of echoes from the tissue interfaces within the patient. The position, amplitude and phase of the echoes or backscatter create one or more acoustic lines or regions, and one or more emissions can be directed at different locations and directions to form a frame or image of the underlying structures. Mapping of amplitudes in an image is called a B-Mode image.

Other methods, such as Doppler methods, are based on measuring the change in position, phase or frequency in the returned echoes. Moving structures and blood flow cause a Doppler shift. Other methods, such as elastography, are used where a small displacement is made in the tissue and the displacement is measured in very small increments to extract mechanical properties. These displacements may be caused by a mechanical push, a vibration, or an acoustic push, which is called a radiation force push.

Screening for breast cancer is currently mostly performed by mammography, an x-ray technique, because of its ability to reliably image calcifications. Microcalcifications are present in clusters in 60-80% of breast cancers, and are a reliable indicator of benign or malignant lesions. Microcalcifications sized between 100-microns and 200-microns, in clusters of greater than five, comprising calcium hydroxyapatite (bone), are indicative of cancer, whereas, calcifications of size greater than 500-microns, dispersed throughout the breast and comprising of calcium oxalate, are not indications of cancer.

Mammography is considered the gold standard for breast screening; however, mammography has compromised performance in radiographically dense tissue in the younger patient where the breast comprises more milk producing elements and less fat. This increases the absorption of the ionizing radiation and presents as a whiter image background on which the microcalcifications are presented as white dots. It is estimated that 40% of the U.S. female population has dense breasts, and regulations in most states require that the patient must be informed of alternative methods of screening, such as MRI or ultrasound. This is an even bigger problem in places such as Southeast Asia where it is estimated that over 60% of the female population have dense breasts and there are few resources to detect cancer early.

While an important diagnostic tool, mammography has certain drawbacks. For example, mammography equipment can be expensive, typically priced between $200,000 and $600,000 per instrument. In addition to the high costs, patients are subject to ionizing radiation. For safety concerns, therefore, mammography use is restricted.

SUMMARY OF THE INVENTION

The present invention relates to methods and devices for imaging of microcalcification particles using ultrasound. The methods and devices for imaging of microcalcification particles using ultrasound are utilized as mechanisms of providing indicators of cancer. Embodiments of the invention may be applicable to the imaging and or detection of nearly any particle with a large acoustic impedance variation from the surrounding media.

A characteristic of fast-growing tissues and some cancers is that they produce small, 100-micron to 200-micron diameter ellipsoidal deposits of bone, or more specifically, calcium hydroxyapatite, commonly known as microcalcifications. These particles are dense, and their presence in localized clusters, and their detection, is performed by mammography (an x-ray technique) to diagnose the presence of breast cancer.

These microcalcification particles have a large acoustic impedance difference from the surrounding tissue and produce intense echoes, but due to their small size, the echo energy detected at the transducer is small and can be difficult to discriminate in B-Mode (or echo amplitude) from the backscatter of the surrounding tissue in the breast.

The acoustic impedance of tissue is approximately 1.5 and the microcalcification is approximately 8, and this results in >47% of the energy of the transmission pulse that impacts the microcalcification to be reflected, and, in doing so, imparts significant energy into the particle which is excited into vibration. And, based on the energy imparted and the density or momentum variations, can cause the particle to oscillate differently from the surrounding tissue. This vibration, when encountered by pulses from the latter part of the transmit packet, will cause changes in the fundamental and harmonics or chaos in the backscatter.

If the transmit packet contains enough pulses, at a point proximal of the microcalcification, the echoes returning to the transducer from a microcalcification may be considered as counter propagating waves to the latter forward propagating waves of the transmit packet and these waves will interfere with each other and create chaos in the acoustic wave at the point where they overlap.

The particle, being spherical and of different density, and if approximately the size of the interrogating wave, will cause a non-isotropic distribution in the reflected energy with a bias in the direction of the pulse's direction. This will cause greater echo amplitude at the receiving transducer than the normal d2 distribution of echoes from the tissue. This effect is demonstrated if the transmission is at approximately 4-megahertz, so the second harmonic is at 8-megahertz, and the wavelength is approximately the size of the microcalcification particle which is approximately 150-microns diameter.

Acoustic lines may be separated temporally by the round-trip time of flight to and from the region of interest plus the ultrasonic scanner's reset time required to emit another pulse, and this is typically 5 to 500-microseconds in total for B-Mode imaging. In this time, nearly any movement in a stationary organ is either small enough to be insufficient to cause any significant difference in the backscatter from the tissues, or linear enough to remove. An 8 MHz sound wave in tissue is approximately 0.2 mm, and at a PRF of 500 us this would require a velocity of +/−20 cm/s to begin to alias. These velocities can be present in some tissues such as the heart, circulatory valves or in blood flow, but can also easily be discriminated. Elevational movement can change the superposition of backscatter to induce large changes in the signal and could be discriminated via filtering or operator instruction or the use of a >1 d array.

If the acoustic lines intersect a microcalcification, they will differ at the point of the microcalcification because of the chaotic motion of the microcalcification particle and or the interaction of the counter-propagating waves at the microcalcification. The chaotic motion has not been found to have any synchronicity with the Pulse Repetition Frequency, or repeatable features, so a difference in the amplitude or phase and harmonics between any two or more acoustic lines can be detected at this point.

The difference between two or more sequential acoustic lines gathered along the same vector, within a few hundred microseconds, will be substantial at any microcalcification and insignificant during their transit through soft tissue. These methods will be used to visualize microcalcifications in a new method proposed to be called CA-Mode.

As used herein, the term "insonification" is defined as flooding of an area with carefully-controlled sound waves (acoustic energy), typically along a vector in a specific direction or focused at a specific location. There are various methods currently in use, such as focused transmissions, limited diffraction beams, plane waves, and diverging waves.

As used herein, the term "Acoustic Line" is defined as the data set that results from a round trip transmission of an insonification and the collection of digitizations of the received backscatter (echoes) held in a memory. These are usually 4096 to 8192 digitizations, 20-bits deep, held in a memory for further processing.

As used herein, the term "Transmission or Transmit Pulse" is defined as an acoustic pulse, made by applying a voltage pulse or range of voltage pulses into one or more transducer elements to generate acoustic insonification.

As used herein, the term "Transmit Packet" is defined as multiple transmit pulses which comprise one insonification.

As used herein, the term "Pulse Repetition Frequency (PRF)" is defined as the number of transmit pulses emitted by the transducer over one second of time. This is limited by the time of flight to the depth of interest. It is typically measured as pulses per second. In medical ultrasound, the typical range of PRF varies between 250 and 50,000.

As used herein, the term "Acoustic Impedance, (z)" is defined as the ratio of acoustic pressure to wave front speed, and is an inherent property of the medium and of the nature of the wave. Acoustic Impedance (z) may be calculated by the medium's density (p) and the speed of sound in the medium, i.e. z=pv. The SI unit of acoustic impedance is the Rayl. For tissue z=1.5 mega Rayls, for a micro-calcification z=8 mega Rayls.

As used herein, the term "Acoustic Reflection" is defined as ultrasonic waves which are reflected at boundaries where there is a difference in acoustic impedances (z) of the materials on each side of the boundary. The reflection expressed as a percentage is: $R=((z_1-z_2)/(z_1+z_2))^2$.

As used herein, the term "Backscatter" defines the echoes that return to the transducer from the tissue, and are made from millions of multiple reflections of the insonification from tissue interfaces and organ boundaries.

As used herein, the term "Magnitude of Differences" is defined as the recorded change in the signal extracted by one or more mathematical steps in one or more recorded samples corresponding to a spatial location. Differences can be calculated from a variety of mathematical operations in a specific time or frequency or other domain. Some examples (not limiting) are:

1. Subtraction of the amplitude of two or more RF or demodulated signals corresponding to the same spatial location from different transmissions. The second derivative through slow time is the preferred embodiment as it is able to reduce or eliminate most linear motion artifacts.

2. The difference in magnitude of the difference from 1, where received signals are from the same location for both sets, but transmit is changed between sets either in power, location or frequency. The difference between the signals from two or more transmit receive events where the transmit is focused at location 1 vs. the difference between the signal from two or more transmit receive events with the transmission focused at location 2, 3, 4, etc.

3. The difference in cross correlation coefficients between transmit receive events.

4. The difference in the phase of data between two transmit receive events.

5. The difference in the magnitude between two or more frequencies in the same or different transmit receive events, e.g. fundamental vs. harmonic, frequency differences.

6. The difference in the amplitude or phase of the signals in a frequency domain, e.g. Fourier transform, z transform, etc.

In certain illustrative embodiments of the invention, a non-invasive and nondestructive method of identifying particles with a large acoustic impedance variation, such as microcalcifications, iron deposits, or microbubbles in tissue or cracks, crystals or other impedance changes in a material as in nondestructive testing, may include a method comprising, in any combination, the steps of:

A. Using an ultrasonic imaging system to transmit and receive acoustic waves in an area of tissue or a material.

B. Optionally using the ultrasonic system in (A) to form B-Mode images of the underlying structures in the tissue or material under test. And optionally time splicing the modes by lines, groups of lines, or frames in order to simultaneously image Bmode and Particle impedance variations in the same spatial locations.

C. Using the ultrasonic imaging system in (A) to transmit acoustic waves to stimulate particles of a large impedance difference to spatially displace in an oscillation.

D. Generating sets of coherent spatially overlapping receive data from the transmitted wavefronts in (C) captured by the ultrasonic imaging system in (A) to form an image of particles with large acoustic impedance differences from the background tissue or material.

E. Using a short transmitted waveform for the stimulation pulses in (C) comprised of 2 or more cycles to stimulate a particle to oscillate and build up energy in oscillations of the particle, relative to the background tissue or media, to a detectable displacement level. The stimulation pulse may be comprised of one or more of the following methods:

a. Two or more cycles of a single frequency.

b. Two or more cycles using two or more frequencies such as a chirp or pulse compression technique.

c. Pulse inversion techniques with two or more cycles.

d. Splitting the aperture into two or more Sub apertures with one or more varying frequencies, power, cycle counts, or directionality.

e. Using Limited diffraction focusing techniques such as Xbeams or Bessel beams.

F. Collecting and forming an ensemble of two or more received signals from a given spatial location with at least one received signal being reflected from a stimulation pulse from the ultrasonic waveforms transmitted in (E) using one or more of the following methods:

a. Focusing the transmit wavefronts in (E) at a single spatial location b. Focusing one or more transmit wavefronts at a spatial location and one or more sets of receive data from a transmit focus synthetically created at the same point.

c. Using a similar waveform to the stimulating pulse in E but at a lower power such that the particle is induced to oscillate less or not at all.

G. Calculating the displacement between the signals in (F) at one or more spatial locations using one or more of the following methods:

a. Taking the derivative of the RF signal across the ensemble.

b. Taking the derivative of the demodulated RF signal across the ensemble.

c. Using a correlation method, 1 d, 1.5 d, 2 d auto/cross correlations or covariance methods between signals across the ensemble d. Using a frequency domain transform over a part of the transmit pulse length and comparing the phase between ensembles.

e. Using a frequency domain transform across the ensemble at the same or shifted spatial locations.

f. Using a two or higher dimensional frequency domain transform over one or more spatial dimensions and the ensemble dimension g. Calculating an eigen value/vector decomposition such as PCA to separate static and oscillating signals.

H. Using the displacements to identify particles with a large impedance difference from the background tissue by the variation in the displacement across ensembles at one or more spatial locations. The method comprising one or more of the following methods:

a. Calculating the derivative of the displacement from (Ga or Gb) at distinct spatial locations across the ensemble. IE The second derivative of the RF signal or the demodulated RF signal across the ensemble.

b. Calculating the second derivative of the phase at distinct spatial locations across the ensemble. IE the derivative of (Gc)

c. Thresholding or filtering the magnitude in (a or b) using the magnitude of the received signal at the same spatial location or surrounding spatial locations derived from the reflections received in (B), (D), (F) or in a separate imaging interrogation method.

d. Thresholding or filtering the magnitude in (a or b) using the first derivative of the received signal at the same spatial location or surrounding spatial locations derived from the reflections received in (B), (D), (F) or in a separate imaging interrogation method.

e. Comparing displacements from transmitted waves of varying: power, aperture size, active aperture, spatial focal point location or focus quality.

f. Comparing displacements from the same spatial location across one or more ensembles where the transmissions are focused at spatially distinct locations.

g. Comparing the first derivative of the rf or demodulated signal or the phase difference from two or more received signals over the pulse length of the reflections from a spatial location.

h. Comparing the first derivative of the rf or demodulated signal or the phase difference from two or more captures over the pulse length of the reflections from a spatial location, where the transmit focus points are different, or synthetically created for the same location.

i. Comparing the frequency spectrum in (Gd) across the ensemble.

j. Comparing the frequency spectrum in (Ge) across the pulse length.

k. Comparing the frequency spectrum in (Ge) with one or more offset samples in the pulse length across the ensemble.

l. Comparing the frequency spectrum in (Ge) with offset vectors through the ensemble in varying directions.

m. Comparing the Eigenvalue magnitude distributions in (Gf)

n. Comparing the eigenvector directions with their respective eigenvalues in (Gf).

o. Calculating the magnitude, envelope, or amplitude of the second derivative signals in (Ha) or (Hb).

p. Calculating the sum of the magnitude, envelope, amplitude or absolute values of the signals obtained in (Ha) or (Hb).

G. Optionally Removing particles with a velocity that would cause the signal to alias using one or more of the following methods:

a. Comparing the output at one or more spatial locations from one or more of the methods in (G) or (H) where the stimulation pulses have different focal spatial locations. Eg:

i. Stimulation transmit pulse focused at location 1, calculate displacement from receive data from location 2 between two or more stimulation transmit pulses or at least one stimulation transmit pulse and one or more similar transmit pulses with less power at location 2.

ii. Stimulation transmit pulse focused at location 2, calculate displacement from receive data from location 2 between two or more stimulation transmit pulses or at least one stimulation transmit pulse and one or more similar transmit pulses with less power at location 2.

iii. if (Gai)>x % of (Gaii) disqualify as aliasing velocity.

iv. (Gai) and (Gaii) may be formed in the same ensemble and selectively compared in (G) or (H) to accomplish the same qualification.

b. Comparing the output from one or more of the methods in (G) or (H) with an output from one or more methods in (G) or (H) calculated from reflected signals from transmissions intentionally below the stimulation threshold of the particles oscillations such as in (Fc). Eg:

i. Stimulation pulse focused at location 1, calculate displacement from receive data from location 1 between two or more stimulation transmit pulses or from one or more stimulation transmit pulses and one or more similar transmit pulses with less power at location 1.
ii. Transmit low power pulse two or more times covering location 1, and calculate displacement from receive data from location 1 between pulses.
iii. If (Gbii)>x % (Gbi) disqualify as aliasing velocity.
iv. (Gbi) and (Gbii) may be formed in the same ensemble and selectively compared in (G) or (H) to accomplish the same qualification.

In certain illustrative embodiments of the invention, a method of visualizing microcalcifications in a tissue or organ of a mammal, may comprise the steps of, in any combination:

(a) using an ultrasonic imaging system to transmit and receive acoustic waves to an area of a tissue of a mammal;
(b) delivering acoustic waves to stimulate microcalcifications to spatially displace;
(c) generating sets of coherent spatially overlapping receive data from transmitted wavefronts in step (b) captured by said ultrasonic imaging system to form an image of microcalcifications in said tissue or organ of a mammal;
(d) using a short transmit packet insonification for the stimulation pulses in step (b), said stimulation pulses comprised of transmit pulses forming 2 or more compression and rarefaction cycles to stimulate the microcalcifications to displace or oscillate and build up energy in displacements of the microcalcifications, relative to the background tissue or media, to a detectable displacement level;
(e) collecting and forming an ensemble of two or more received signals from a given spatial location with at least one received signal being reflected from a stimulation transmit pulse packet insonification transmitted in step (d);
(f) calculating displacement between signals in (e) at one or more spatial locations; and
(g) using displacements to identify the microcalcifications with a large impedance difference from said background tissue or said material by a variation in the displacement across ensembles at one or more spatial locations.

In certain illustrative embodiments of the invention, a method of visualizing a microcalcification in tissue or organ of a mammal may comprise the steps of: using ultrasound imaging technology to transmit three or more insonifications and receiving signals from said insonifications and taking the second derivative through slow time to produce a magnitude or envelope value at given spatial locations.

Accordingly, it is an objective of the invention to teach methods of medical imaging.

It is a further objective of the invention to teach devices related to medical imaging.

It is yet another objective of the invention to teach methods related to ultrasonic medical imaging.

It is a still further objective of the invention to teach devices related to ultrasonic medical imaging.

It is a further objective of the invention to teach devices for imaging microcalcification particles using ultrasound.

It is yet another objective of the invention to teach methods for determining microcalcification using ultrasound.

It is a further objective of the invention to teach methods for imaging microcalcification particles using ultrasound.

It is yet another objective of the invention to teach devices for imaging microcalcification particles using ultrasound as indicators of cancer.

It is a still further objective of the invention to teach methods for imaging microcalcification particles using ultrasound as indicators of cancer.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DETAILED DESCRIPTION OF THE INVENTION

Figure 1:
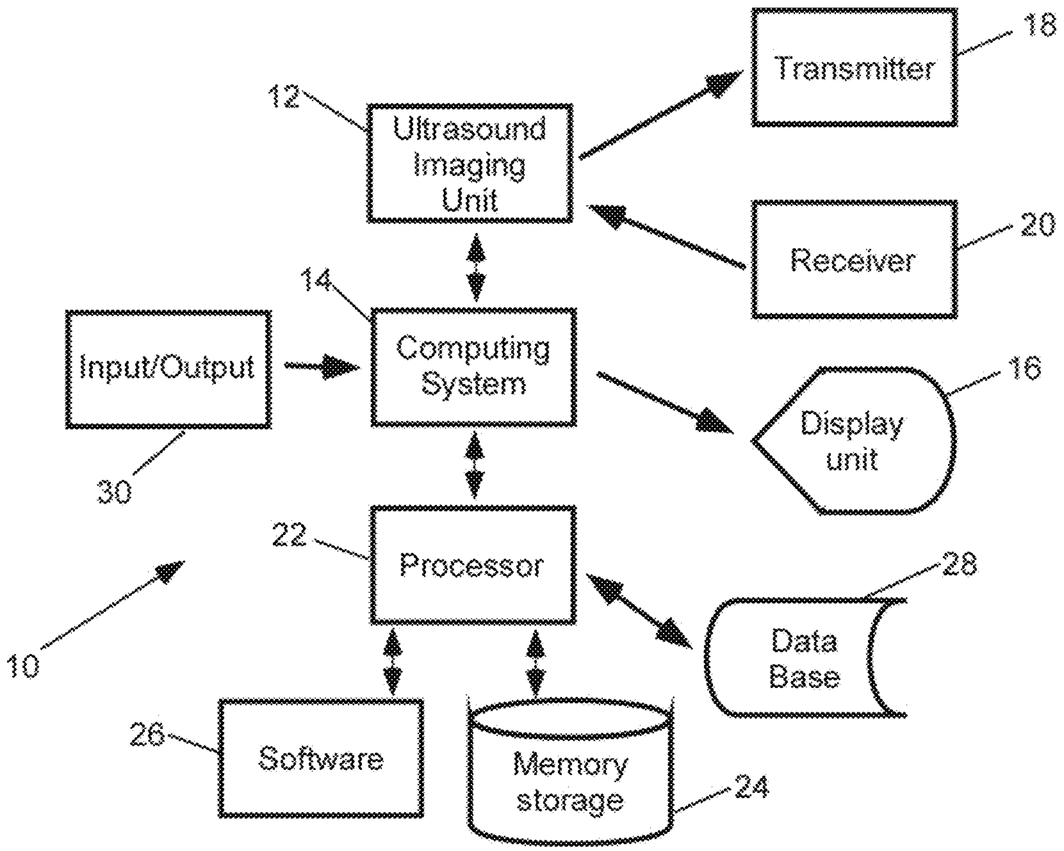
FIG. 1 is a schematic representation of an illustrative example of an imaging system for visualizing microcalcifications using ultrasound.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Many organs and parts of the body are comprised of soft tissue superior to the bone structure such as breast, thyroid, and liver. Medical ultrasound is used diagnostically to examine and diagnose diseases and conditions in soft tissue. Ultrasound is the predominant method of visualizing the morphology in soft tissues, and it depends on differences encountered at variations in the density, speed or sound (acoustic impedance) at cellular and organ boundary interfaces, which is a property of the tissue.

Acoustic impedance (Z) depends on the density of the tissue (which may be expressed in kg/m3) and the speed of the sound wave (usually expressed in m/s), and they are related by $Z=\rho\times c$ and is described as how much resistance an ultrasound beam encounters as it passes through tissue.

An ultrasound transmit pulse's ability to transfer from one tissue type to another depends on the difference in impedance of the two tissues. If the difference is large, then more of the transmit pulse's energy is reflected.

The amount of reflection that occurs is expressed by: Reflection fraction (percentage)$=[(Z_2-Z_1)/(Z_2+Z_1)]^2$, where $Z_1$ and $Z_2$ represent the impedance in tissue 1 and tissue 2, respectively.

Examples of acoustic impedance for organs of the body are: fat $1.34\times10^6$, water $1.48\times10^6$, kidney $1.63\times10^6$, blood $1.65\times10^6$, liver $1.65\times10^6$, muscle $1.71\times10^6$, and bone $7.8\times10^6$.

From the equation above, less than 1% of sound is reflected at a fat-liver interface and 47% is reflected at a muscle-bone interface or a microcalcification.

If the sound wave is not perpendicular to a surface, some of the sound wave will be reflected away from the transducer in accordance with Snell's law.

In a breast, the only variations in acoustic impedance is expected to be minor between the pectoral muscles, ligaments, fat, and glandular tissue which present a variation of 1.34 to 1.71, or as shown above to be less than 1% of the incident energy reflected at these interfaces.

Macrocalcifications, which are defined here to be greater in size than 200-microns, are results of aging, milk production, vascularization changes or past trauma, and are made of calcium oxalate, have a density of approximately 2, are randomly dispersed, and have been found to be not an indication of cancer. The visualization of macrocalcifications can be minimized or eliminated by setting thresholds in the difference values, or by determining the size and or composition of the particles based on the scatterer frequency response, or through other imaging modes such as a B-mode image to determine the size of the particle, and will not be confused with microcalcifications.

In B-Mode (amplitude-based image formation), due to the microcalcifications density (>4) and speed of sound (>8000) will reflect 47% of the energy impinging on the microcalcification. However, the microcalcification's small physical size will reduce its visibility on B-Mode scan in the midst of all the other structure interfaces present in the breast. Microcalcifications can be seen, but the background from the other interfaces is high, so ultrasound is currently not used for microcalcification detection.

The 47% reflection at the microcalcification imparts a momentum into the microcalcification. Due to the momentum not being absorbed but reflected, this momentum is doubled, and is imparted into a relatively small particle. Utilizing acoustic radiation levels that are used and approved by regulatory agencies for B-Mode imaging, it has been found that a microcalcification can be seen to be physically moved by this transfer of momentum, and this can appear to be a positional change on the order of nanometers to microns.

If the Transmit Wave Packet comprises multiple Transmit Pulses, the reflection of the latter pulses of this wave packet will be modulated by the positional movement of the particle from the earlier pulses.

This modulation may be thought of as a non isotropic viscosity damped spring-loaded double pendulum or a damped driven harmonic oscillator, whereby slight variations in position, timing, phase, power, amplitude, jitter or other characteristics of the particle or transmit wave have enough variation to cause instability to manifest in a measurable chaos in the returned signal over multiple cycles. In the preferred embodiment, this difference is taken from three insonifications whereby the second derivative is calculated through slow time at each spatial location, though it can be measured one or more insonifications. In a preferred embodiment there may be a first insonification used to set up reverb in the material to stabilize the response from later insonifications.

As an illustration only, a 4 MHz packet of four contiguous sine waves will be in tissue (approximate speed of sound of 1540 meters per second) ($\lambda=v/f$) 375 microns per cycle greater than 1500 microns for the wave packet, or expressed in time as a 1-microsecond aberration, i.e. the particle will move in response to the first cycles, and this can be observed by the later cycles as shifted in position. So, the latter cycles of the transmit wave packet may be frequency modulated by the movement of the particle from the energy imparted by the first cycles of the ensemble. This is of interest as, in the soft tissues of the breast, there are no other mechanisms to cause any abrupt aberration of transmit packet or harmonics generated by the wave's transmission.

Harmonics are generated by the high-pressure portion of the wave traveling faster than the low-pressure portion, resulting in distortion of the shape of the wave. This change in waveform leads to the generation of harmonics (multiples of the fundamental or transmitted frequency) from a tissue. These harmonic waves that are generated within the tissue increase with depth to a point of maximum intensity (focus point) and then decrease with further depth due to attenuation. This generation of harmonics is continuous and not an abrupt disturbance as described above as occurring at a microcalcification.

The immediate environment of the microcalcification is also expected to be complex in that microcalcifications are known to form on the surface of a duct lobule (milk producing structure) against other breast structures. Its "spring structure" is not expected to be isotropic, and its movement is not expected to be in the direction of insonification. Thus, the microcalcification, if interrogated within its damped vibrational period, will not be expected to be in the exact same location as its first insonification by an interrogating pulse.

Also, at the microcalcification, the reflection is as shown above to have 47% of the energy of the incoming ultrasonic wave. In a packet of multiple waves, the latter pulses are expected to first encounter the reflected earlier pulses of the packet in the space just proximal to the microcalcification. This is a space which could be described as a volume of counter propagating waves. Here, the reflections of the earlier pulses will interfere with the later pulses of the transmit wave packet. This space is defined by the frequency of the pulse packet and the number of pulses in the packet. This space may be extended by extending the number of cycles in the transmitted packet. At points where a compression from an incoming sine pulse coincides with a reflection compression, the compression will be amplified so the pulse will have a higher speed of sound. Similarly, with rarefactions and compressions interacting with rarefactions, the interaction will be complex and be expressed in the time of flight of the received echoes from that point, as well as in the harmonic power and phase relative to the fundamental frequency. This interaction is dependent on so many microscopic factors it could be best described as a point of chaos. We have not found, and would not expect to find, the same data from this location, even if that time between acoustic lines is less than 100-microseconds.

Thus, we have not found any set of two acoustic lines which intersect the microcalcification to have the same backscatter at the point of the microcalcification, or just proximal to the microcalcification, when enough power has been used to excite the microcalcification. The microcalcification may be modeled by thinking of it as a hard spherical particle held in its position by multiple springs to the surrounding tissue, with anisotropic spring coefficients and damping viscosities. A simplified version of this can be thought of as a double pendulum with starting points that are nearly identical but after multiple swings(transmit cycles within the transmit packet) begin to detectably separate when enough energy is provided. This chaos appears to exist for about a microsecond.

Providing nothing is spatially moved, all points in the rest of the acoustic lines are identical in multiple samplings. Putting a chasing transmit wave at some delay to the excitation packet can detect that the particle is back in its original location after variable amounts of time. Specialized interrogation pulses determined that the particle was in an identical location on each interrogation after some time, EG sending a 4 cycle transmit packet with a 0.1-10 us delay and then another single cycle where the difference in the trailing cycle between insonifications reduces below the noise floor, ie (+−+−+−+−0000+−, +−+−+−+−0000000+−, +−+−+−+−0000000000000000+−). The time required for the particle variations to dissipate may also be used to calculate certain characteristics of the particle such as size, density, and impedance.

The problem of visualizing microcalcifications is solved by exciting the locations of the microcalcification, by a multi-pulse transmit or acoustic packet of an acoustic line, into an excited chaotic state and comparing the received signal from a given spatial location over multiple transmissions. The acoustic lines will differ at the point of the microcalcification. The comparisons are best found by simple subtraction of the acoustic lines ($2^{nd}$ derivative), but other methods used include cross correlation, pulse inversion, autocorrelation, Frequency domain operations such as phase variance, doppler variance metrics, difference of squares, etc. The preferred embodiment is subtraction due to simplicity and speed. The methods of visualizing and/or detecting microcalcification described herein may be used or applied to any tissue, such as a breast tissue, organ, or other anatomical structure where possible of a mammal, preferably a human. It is also noted that while the methods and devices are described as visualizing and/or detecting microcalcifications, other microparticles may be detected as well such as (but not limited to): iron deposits in certain types of breast cancer, kidney stones, bone fragments, contrast bubbles, bubble defects in materials, surface defects/cracks, or material impurities, etc.

The transmit packet of multiple pulses may include a single pulse, which is a lower signal to noise, to over 32 pulses, and currently four pulses is the preferred embodiment due to the tradeoff between resolution and SNR. Longer transmit packets can be used to better characterize the particles material properties and may be used in conjunction with or in place of the shorter imaging/detection pulses. The frequency of the transmit pulse is dependent on the transducer characteristics. For microcalcification particles of 100 to 200 microns, 1-15 MHz fundamental transmit frequency creating a second harmonic of 2-30 MHz may be optimal for power, penetration and having the most interaction with the particles. Interaction with a 100-200-micron particle may be optimized with a wavelength that is approximately of these dimensions. A powerful transmission of a relatively low frequency of 4 MHz can be focused to any depth in the breast, generating harmonics which will add to the interaction with the microcalcification.

FIG. 1 is a schematic representation of an illustrative example of an imaging system for visualizing microcalcifications using ultrasound, referred to generally as microcalcifications imaging and detection system 10. The microcalcifications imaging and detection system 10 may include one or more of the following, in any combination of components: an ultrasound imaging unit 12, a computing system 14 for receiving or processing ultrasound images, and a display unit 16. It is noted that any of the components of the microcalcifications imaging and detection system 10 can operate via wired or wireless connections.

Ultrasound technology is well known in the art, and any imaging device known to one of skill in the art may be used. The ultrasound imaging unit 12 may include a transmitter 18, such as one or more electro-acoustic elements for transmitting acoustic energy and a receiver 20, such as one or more electro-acoustic elements receiving acoustic energy. The one or more electro-acoustic elements may be, for example, a piezoelectric ceramic (pzt or other piezoelectric compounds, can be single crystal or composite), or polymer, such as Polyvinylidene fluoride or polyvinylidene difluoride (PVDF), a capacitive micromachined ultrasonic transducers (CMUT) or movable electrode in piezoelectric ultrasonic transducers (PMUT), or even electro-magnetic like a speaker, etc., any transducer capable of converting electric or magnetic energy into acoustic waves and some receiver capable of converting sound waves into electric signals. These can vary in size, shape and frequency. This can be done with a single element or array of elements. Arrays can be annular, linear, convex, concave, 1 d, 1.25 d, 1.5 d, 1.75 d, 2 d arrays (multiple rows of elements), etc.

The computing system may include a computer having a processor 22, memory/storage 24, software 26, and any other hardware necessary to perform preferred functions such as, but not limited to, microcalcification detection. The memory/storage 24, and/or software 26 may include the necessary instructions for microcalcification detection. The processor 22 may include general purpose central processing unit(s), application specific processors, and logic devices, as well as any other type of processing device, or combinations or variations thereof. Instructions for microcalcification detection can direct the processor 22 to carry out any of the processes described herein.

The memory/storage 24 may include any computer readable storage media readable by the processor 22 and capable of storing software 26, including instructions for microcalcification detection. Memory/storage 24 may include volatile and non-volatile, removable and non-removable media, implemented in any method or technology for storage of information, such as computer readable instructions, data structures, program modules, or other data. Illustrative examples of the memory/storage 24 may include storage media, including random access memory (RAM), read only memory (ROM), magnetic disks, optical disks, CDs, DVDs, flash memory, solid state memory, phase change memory, or any other suitable storage media. Certain implementations may involve either or both virtual memory and non-virtual memory. In no case do storage media consist of transitory propagated signals. In addition to storage media, in some implementations, the memory/storage 24 may also include communication media over which software may be communicated internally or externally. The memory/storage 24 may be implemented as a single storage device, but may also be implemented across multiple storage devices or subsystems co-located or distributed relative to each other.

The microcalcifications imaging and detection system 10 and methods thereof may further include a database 28 having one or more ultrasound images stored therein. The microcalcifications imaging and detection system 10 may include Input/Output devices 30, such as a keyboard, mouse, joystick, light pen, scanner, touchscreen. The display unit 16 may include a monitor or a visual display unit, such as an LCD monitor. The microcalcifications imaging and detection system 10 may be configured as a single stand-alone unit. Alternatively, the microcalcifications imaging and detection system 10 may be part of a network of connected computer systems or other computing machines, including as part of servers or cloud based computing systems. The microcalcifications imaging and detection system 10 may be a single desktop computer, a laptop computer, a tablet, a phone, a server, or any other machine capable of executing a set of instructions (sequential or otherwise) that specify actions to be taken by that machine, as well as multiple machines that individually or jointly execute a set (or multiple sets) of instructions to perform any one or more of the methods described herein.

The microcalcifications imaging and detection system 10 and methods thereof may include or be configured to utilize a microcalcification identifier circuit. The microcalcification circuit may include digital/analog processing done to differentiate the background tissue from the microcalcification. Such processing is preferably done in software on digital signal recordings, but may be accomplished in the analog domain. In a preferred embodiment, the simplest form would be digitizing the echo signals from a given spatial location from two or more transmit events, and then taking the magnitude of the subtraction (derivative through slow time) of the RF signals. This can be similarly achieved through many mathematical operations on the same echo data, such as by correlations, phase, or amplitude differences, and can be performed on demodulated data, frequency domain data, beam formed or channel data. This can be done by taking the eigenvalues of the covariance matrix of the received RF lines or channel data corresponding to a given spatial location and comparing the relative magnitudes of the dominant eigenvalues, such as a ratio of the magnitude of the first N eigenvalues, or comparing the angle of the eigenvectors from covariance matrices from different groupings of the data.

The microcalcifications imaging and detection system 10 may include or be configured to utilize a microcalcification identifier circuit that uses the estimated magnitude difference to distinguish microcalcifications from background using one or more of:

1. The magnitude of the difference in amplitude between signals or combinations of signals from the same location or delay. The magnitude of the difference can be determined as the absolute value or the envelope of the signal generated from the first or second or higher derivative through slow time, i.e. first derivative=((line 1 sample 1)−(line 2 sample 1)); second derivative=((line 1 sample 1−line 2 sample 1)−(line 2 sample 1−line 3 sample 1). This can also be accomplished using Pulse Inversion Harmonic techniques. The magnitude of the difference can be determined as the ratio of amplitude difference between the eigenvalues from the covariance matrix from difference groupings of signals received from the same spatial location. The magnitude of the difference can be determined as the amplitude difference between the demodulated signals, or can be the amplitude of the derivative of the phase between frequency components from one or more received sets. The Second Derivative is favored as is naturally removes significant portions of linear displacements and incorporates the magnitude of the signal whereas phase techniques are more vulnerable to noise and need to factor the magnitude of the signal back in. Eigen decomposition can factor in the magnitude into the largest eigenvalues but is significantly more calculation than simple subtractions.
2. The magnitude of a phase or frequency shift between signals or combinations of signals from the same location or delay or between cycles from the same location in one or more insonifications. This can be mathematically represented by phase information from a Hilbert transform, a correlation, frequency domain transform (Fourier, Hartley, z), demodulation, etc., however the phase will change as the particle moves relative to the incoming acoustic waves and background tissue.

3. The magnitude of the difference between sets of difference data from the same receive location or delay from different transmit frequencies and or locations. This difference determination may be performed to distinguish from background variation levels in tissue or blood causing false positives. For instance, a transmit packet can be focused to one location near the microcalcification, and then somewhere spatially different, or with different frequencies, or sub-apertures, or power levels, etc. The power applied to sub-aperture sections could be changed to impart a different insonification power vector to get the microcalcification to oscillate in different directions to induce a difference in the received signal. This can be used to distinguish tissue movement, large boundary echoes, blood flow, or blood vessels from smaller particles, as the particle exhibits a much higher variation between received data sets when the transmit power is highly focused at it vs. other background tissues. Spatially changing the location of the source of the transmit can also be used in sizing the particle. A boundary layer in tissue or small blood vessel would be a smooth ramp in the magnitude of the difference between difference signals corresponding to the magnitude of the insonification at the given location, while a microcalcification or small particle would exhibit a (nonlinear with respect to the insonification power at the given spatial location) large change in the magnitude difference between difference signals when the power in the acoustic wave is changed. The power can be modulated by changing the pulse characteristics, such as aperture, voltage levels, applied waveforms, sub-aperture variations, focal point spatial location, etc.
4. The magnitude of the difference in amplitude or phase of signals in the time or frequency domain from multiple transmissions. Taking the difference in amplitude of the signals can be a simple subtraction of the amplitude values in the RF, or demodulated data, or frequency domain data. The difference in phase can be taken by subtracting the phase between repeats, i.e. phase=arctan (I/Q), like the variance in a Doppler processor. The I and Q can be RF, or demodulated or frequency domain representations, or eigenvectors of the covariance matrix, etc.
5. The magnitude of the difference in amplitude or phase of signals in the time or frequency domain from a single transmission where the signals are separated in frequency, such as the fundamental vs. harmonic, or multifrequency transmissions such as a chirp, or multiple elements emitting different frequencies. The difference in the amplitude or phase values can be performed by taking the echo signals corresponding to one or more cycles of the transmit, and then comparing them to other cycles of the transmit. EG 8 cycles (c1, c2, c3, c4, c5, c6, c7, c8) can then be compared to the amplitude and/or phase information from varying cycles, such as the difference in amplitude from cycle 1 to cycle 8, or the ratio of power in the fundamental and harmonic signals from cycle 1 and 8, or groupings of cycles (c1c2 vs. c3c4, c1c3c5c7 vs. c2c4c6c8, etc.)
6. The magnitude of the difference in amplitude or phase of signals acquired from different transmit events at varying power levels. For example, transmit a packet at power level 1 and receive the echo data, and transmit a packet at power level 2 and receive the echo data. Then, taking the difference in amplitude or phase between received signals, or between groups of signals. A preferred embodiment might include taking multiple transmit receive data points at each power level and comparing the magnitude of the differences between the power levels. To improve frame rates, multiple locations may be interrogated at a lower power level at a time using techniques such as pixel based beamformers, multi beamformers, plane wave imaging, weakly focused waves, diverging waves, etc. The power levels may be interleaved to reduce temporal artifacts such as pulsatile blood flow or vessel wall motion, i.e. p11, p21, p12, p22. The difference can then be calculated in many ways such as abs(p11−p12)−abs(p21−p22) or as a ratio abs(p11−p12)/abs(p21−p22), or simply thresholding based on variation detected at lower power, etc. The power can be changed by altering any of the multiple characteristics of the transmit such as voltage, phase, aperture, drive current, sub aperture patterns, waveforms, frequency, focus point, etc.
7. The magnitude of the difference in amplitude or phase of signals acquired from different transmit events with the aperture divided into one or more sub-apertures with varying phase, amplitude or frequency. For example, change the f number (aperture size), change the focus spatial location, split the aperture into sub apertures and change the waveform, phase, delays, pulse width modulation, phase jitter, voltage levels, current drive levels, etc. A transmit aperture could be increased or decreased even 1 element on a sub aperture, and then move that decrease around on different elements to get the microcalcification to oscillate differently. This may be accomplished by hitting the microcalcification with more power on one side, causing it to oscillate in that direction more. The pattern can then be changed to impart more power on the other side to get it to oscillate in a different direction to increase the difference in received signal.
8. The magnitude of the difference in amplitude or phase of signals acquired from different transmit events with a jitter or phase or timing or amplitude variation on different elements or sub apertures. This can be accomplished by slight variations in the transmitted signal, which cause oscillations to significantly differentiate the received signal. At 4 MHz, transmit signal jitter of 100 picoseconds between elements would correspond to 0.04% timing variation. This can be induced intentionally by changing the transmitted waveforms amplitude, phase, or delay.
9. The magnitude of the difference in amplitude or phase of signals corresponding to the same spatial location in the tissue acquired from different transmit focus depths or lateral locations or directions. Beam steering can be digitally accomplished on an array, where an operator can focus a transmission in the same location but have it originate from a different spatial aperture. The microcalcification exhibits significant oscillation differences based on the transmission, so transmitting to a focal point spatially different can induce large changes in the magnitude difference at the same receive point. Multi line receive beam formers can create and receive data from multiple spatial locations from any transmit location or pattern. Taking the difference of the magnitude difference as the transmit focus is spatially moved closer or further from the receive point is a good way to discriminate the microcalcifications. For example, transmitting to a location close to the microcalcification will cause it to oscillate more than transmitting to a location further away, and the difference in the oscillation is much larger than for other tissue boundaries. If there are two spatial locations and the microcalcification is located at spatial location 1, focusing the transmit at location 1 will result in large variations between repeats of the acoustic line. If the system or an operator focuses at location 2, the variations will rapidly decay based on the relative power insonifying location 1.

10. The ratio or magnitude of the differences between sets of magnitude differences in amplitude or phase of signals from the same or different transmit characteristics such as power, jitter, frequency, focal depth, sub-aperture characteristics such as power, phase, frequency, jitter, etc. This may be accomplished by, for example, focus at location 1, transmit packet with power level 50, repeat multiple times to get a difference signal, focus at location 1, transmit packet with power level 100, repeat multiple times to get a set of difference signals. Compare the ratio of the amplitude of the difference signals between transmitted power levels. This can be done by changing power levels, waveforms, frequencies, aperture size, sub aperture characteristics, etc.
11. A signal processor circuit that forms an image or matrix based on the acquired data, wherein the signal processor circuit identifies the distinguished microcalcifications on an image or in a matrix or spatial location.

The microcalcifications imaging and detection system 10 and methods thereof may include or be configured to utilize one or more echo signatures to form a mapping of the detection of a microcalcification in a given location. The microcalcifications imaging and detection system 10 and methods thereof may include or be configured to utilize two or more echo signatures to form a difference magnitude image or mapping of the detected microcalcifications superimposed on top of a B-Mode image or by itself.

The microcalcifications imaging and detection system 10 and methods thereof may include or be configured to utilize the ultrasound imaging unit 12 to acquire channel data from one or more receive channels via ultrasound received on the one or more channels.

The microcalcifications imaging and detection system 10 and methods thereof may include or be configured to utilize a difference factor determinator, using the acquired data to estimate the signal variation in the data from a given spatial location in frequency or amplitude or phase or time. The difference factor determinator may use a threshold on the difference signals or ratio of difference signals. The threshold or ratio is determined from the amplitude or phase or frequency differences calculated, and may include components of the underlying amplitude or B-Mode image. Such info can be taken from one or more sets of received echo data.

The microcalcifications imaging and detection system 10 and methods thereof may include or be configured so the microcalcification identifier uses an estimated difference to distinguish microcalcifications from background. Such determination may be based on, for example, the level or ratio of the difference between signals. For example, the difference at spatial location A=10⇒ not microcalcification. The difference at spatial location B=1000⇒ microcalcification. The ratio can be determined between sets of difference data.

The microcalcifications imaging and detection system 10 and methods thereof may include or be configured so the processor 22 is configured to form an image based on the data, wherein the processor 22 identifies the distinguished microcalcifications on the image. This may be done, for example, based on the level or ratio of the difference between signals. For example, a difference at spatial location A=10⇒ not microcalcification. Difference at spatial location B=1000⇒ microcalcification. The ratio can be determined between sets of difference data.

Microcalcifications imaging and detection system 10 and methods thereof may include or be configured so the processor 22 can output a visual display distinguishing microcalcifications in an ultrasound view. This output can be displayed as a scan converted image alone or overlaid on the B-Mode image as a color overlay, or can be stored as spatial locations in a computer readable format.

The microcalcifications imaging and detection system 10 and methods thereof may include or be configured so the display unit 16 displays microcalcifications visually distinguished from the background. This may be done by use of a color overlay of the probability a microcalcification exists in a given spatial location. Probability is derived from the difference signals and or other characteristics and combinations of signals.

The microcalcifications imaging and detection system 10 and methods thereof may include or be configured so the use of the difference factor determinator is configured to use the data with respect to a plurality of spatial points having, respectively, an associated transmission event and a delay profile or spatial location. This may be performed by taking the difference values between echoes corresponding to the same spatial locations. This can be done at more than one spatial location per data set, including multi line acquisition beamformers, pixel based beamformers, frequency domain beamformers, etc., at multiple receive depths/delays, lateral locations, etc. The difference factor determinator may be configured to use received data to estimate the difference separately by point with respect to the plurality of points.

The microcalcifications imaging and detection system 10 and methods thereof may include or be configured so the microcalcification identifier is configured to combine estimates of the magnitude difference of each point to identify microcalcifications. Such action may be accomplished by summing or averaging the estimates of the difference at each point or over multiple points. The microcalcification classifier may be configured to use thresholding to distinguish the microcalcifications from the background and other artifacts.

The microcalcifications imaging and detection system 10 and methods thereof may include or be configured so the microcalcification determinator estimates probability of a microcalcification by summing, over multiple transmit packets, a function of the data with respect to a given receive acoustic line and a given time or spatial depth. Such action may also be performed by summing the function over the channels independently.

The microcalcifications imaging and detection system 10 and methods thereof may include or be configured so that data obtained comprises radiofrequency, demodulated, beamformed or channel data, and the difference determinator derives the magnitude from one or more transmission events or from the differences in the composite frequencies (fundamental and harmonics, chirp components etc.).

Figure 2A:
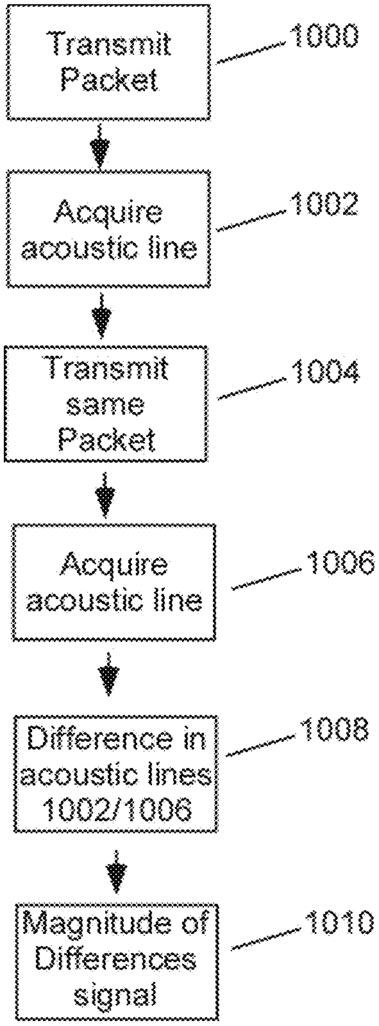
FIG. 2A is an illustrative embodiment of a process for visualizing microcalcifications.
Figure 2B:
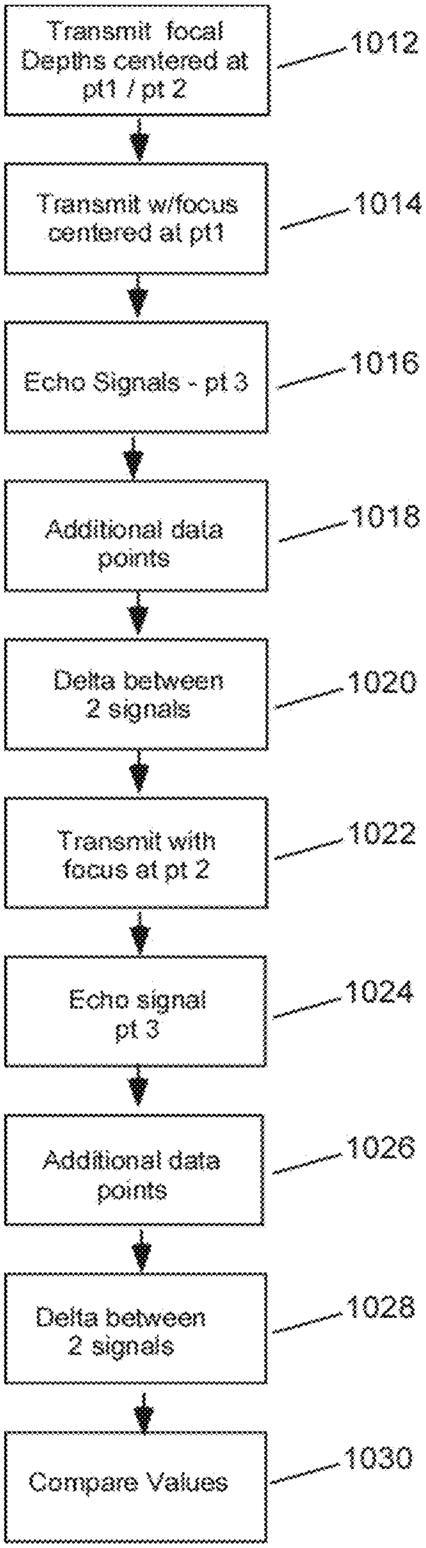
FIG. 2B is an illustrative embodiment of a process for visualizing microcalcifications.
Figure 2C:
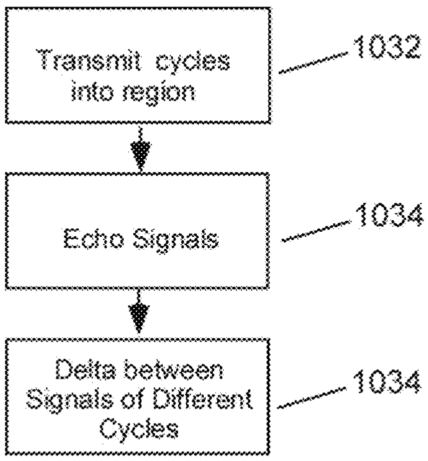
FIG. 2C is an illustrative embodiment of a process for visualizing microcalcifications.

FIGS. 2A-2C provide illustrative embodiments of the visualizing microcalcifications. One or more transmit elements insonify an area of tissue with one or more cycles of acoustic compression and rare fraction (transmit packet). The sound waves interact with the tissue, compressing and stretching it based on the material properties of the tissue. When there is an abrupt change in the acoustic material properties that make up the acoustic impedance, such as a microcalcification embedded in tissue, the tissue and microcalcification will react differently to the acoustic wave, inducing a slight damped harmonic oscillation between the two. This effect can be magnified by increasing the length of the transmit packet by sending multiple compression and rare fraction cycles into the tissue. For example, a sine wave extending over 8 cycles (+−+−+−+− or −+−+−+−+ or +0+0+0+0 or −0−0−0−0 etc.) will have a better signal to noise ratio than a single cycle pulse (+− or −+) or half cycle pulse (+ or −), longer duration pulses can form 'beats' in the difference signal which can be used to characterize mechanical properties of the particle but significantly reduce spatial resolution. The effect can also be observed and/or magnified with coded transmissions, such as (but not limited to) Golay or Barker codes, chirps, pulse inversion techniques, multi-frequency transmissions, sub-aperture variations in the transmit pattern (frequency, phase, power, pulse pattern, etc.) for multi element arrays, acoustic power variations, such as changing the applied transmit voltage, current drive, jitter, pulse pattern, aperture size, etc.

The difference operation can be made in many ways, though the simplest is a direct subtraction between two pairs of received echoes (acoustic lines), RF data with the same transmit receive delays, phase, and spatial location characteristics.

Similar Approaches would Include:

The cross correlation/covariance value between two lines deviating from 1, or −1 in the case of pulse inverted transmissions.

The amplitude difference between the I1 and I2 or Q1 and Q2 or some other combination of demodulated signals, such as the phase angle (arctan(I1/Q1)−arctan(I2/Q2))

The amplitude or phase difference of frequency domain components of the received signal, e.g. Fourier transform frequency component amplitude and or phase variations in the I and Q comparisons of amplitude and or phase between frequency components.

The signal may also be broken up into return cycles that are compared in a single acoustic line response, e.g., the system transmits an 8 sine wave packet into the tissue and on receive, separates each of the returned cycles in time and compares them with each other based on the expected cycle duration. For example, a 4 MHz sine wave sampled at 40 Mhz would cover 10 samples per cycle for a total of 80 samples at 8 cycles. The subsections of the reflected signal can be compared for phase changes from varying oscillations from one or more acoustic lines.

In order to differentiate changes in the signal received from blood flow, a threshold may be used to discriminate tissue vs blood. This may comprise an echo amplitude threshold, a variance based threshold, or a difference based on transmit or receive characteristics, e.g. a pulse packet may be focused at a first transmission depth, some distance away from the microcalcification, and then closer to the microcalcification, and then calculating the change in the difference signal extracted. The microcalcifications exhibit a nonlinear response in the difference signal compared to the background tissue which can be discriminated in the difference signal based on the power in the acoustic wave at the point of the microcalcification.

EXAMPLE 1

Step 1: Transmit a packet, see step 1000, FIG. 2A,
Step 2: Capture receive signal corresponding to a spatial location, see step 1002,
Step 3: Transmit the same packet again, see step 1004,
Step 4: Capture receive signals corresponding to the same spatial location as in step 2, see step 1006,
Step 5: Take the difference between the signals from steps 2 and 4, (this may be repeated multiple times to have more samples), see step 1008,
Step 6: take the magnitude of the difference signal, see step 1010.

EXAMPLE 2

Two transmit packets focused at spatial locations Point 1 and 2, See FIG. 2B, 1012,
Point 1 is shallow to the microcalcification,
Point 2 is at or closer to the microcalcification,
Point 3 is at the microcalcification,
Step 1: Transmit packet focused at point 1, see step 1014,
Step 2: Receive echo signals corresponding to reflections from point 3, see step 1016,
Step 3: Repeat Steps 1 and 2 to have two or more received data points, see step 1018,
Step 4: Take the difference between the two or more signals, see step 1020,
Step 5: Transmit packet focused at point 2, see step 1022,
Step 6: Receive echo signals corresponding to reflections from point 3, see step 1024, (steps 1+2 and 5+6 may be interleaved for collecting data, i.e. step 1,2,1,2,5,6,5,6 or 1,2,5,6,1,2,5,6)
Step 7: Repeat steps 5 and 6 to have two or more received data points, see step 1026,
Step 8: Take the difference between the two or more signals, see step 1028,
Step 9: Compare the difference values calculated from steps 4 and 8, see step 1030.

EXAMPLE 3

Step 1: Transmit a packet into the region of interest, see FIG. 2C, step 1032,
Step 2: Receive echo signals corresponding to each transmitted cycle reflected from the same spatial locations, step 1034,
Step 3: Take the difference between signals corresponding to the different cycles transmitted, step 1036, Taking the Difference:

EXAMPLE 1

Step 1: Transmit packet A,
Step 2: Receive signals corresponding to a spatial location,
Step 3: Repeat steps 1 and 2 four times to capture signals 1, 2, 3, 4 (may be RF, demodulated, frequency domain transformed, etc.),
Step 4: Subtract the amplitude of the pairs to form difference signals and sum/average the magnitudes, abs(1−2)+abs(1−3)+abs(1−4)+abs(2−3)+abs(2−4)+abs(3−4) or abs((1−2)−(2−3))+abs((2−3)−(3−4)) etc.

EXAMPLE 2

Step 1: Transmit packet A,
Step 2: Receive signals corresponding to a spatial location,
Step 3: Repeat steps 1 and 2 four times to capture signals 1, 2, 3, 4, Step 4: Correlate pairs to form correlation value signals, corr(1,2)+corr(1,3)+corr(1,4)+corr(2,3)+corr(2,4)+corr(3,4)

EXAMPLE 4

Step 1: Transmit packet A,

Step 2: Receive signals corresponding to a spatial location,

Step 3: Separate frequency bands from the signal via filtering, demodulation, or frequency domain techniques, Step 4: Compare the amplitude or phase from the different frequency bands from one or more cycles.

EXAMPLE 5

Step 1: Transmit packet A,

Step 2: Receive signals corresponding to a spatial location,

Step 3: Repeat steps 1+2,

Step 4: Separate the received data into a fundamental and harmonic frequency component, Step 5: Compare the amplitude or phase from the different frequency bands and take the ratio of the differences. FIG. 11C (fundamental) and FIG. 11D (harmonic) show the variation is higher in the harmonic frequencies vs. the fundamental.

FIG. 1 shows an ultrasound system with a transmit unit (18) capable of delivering a transmit packet into the tissue, and a receive unit (20) capable of capturing returning echo signals from the tissue. The microcalcification detection circuit may be included in the computing system (14) or processor (22) or offloaded to another processing unit (30). The output of the microcalcification detector may be sent to one or more of: the display (16) stored in memory (24) or a database (28), or offloaded to external storage or processor (30).

FIG. 2A shows one simple embodiment of the technique. 1000 A pulse packet is transmitted into the tissue and the returning signals are captured (1002). This is then repeated one or more times (1004-1006). The received signals are then compared to produce a difference signal (1008). The magnitude of the difference signals are then summed (1010).

FIG. 2B shows an improved version of the process where different transmit characteristics are employed to alter the signal in a specific way that allows a better discrimination of the microcalcifications. In an ideal embodiment of the process, the system would transmit a pulse packet focused at a first location (1014), receive the echo signals from the insonified area (1016), and repeat this process multiple times (1018), and calculate a difference between then signals (1020). Then transmit a second pulse packet focused at a location spatially different from the first, such as deeper into the tissue (1022), and receive signals corresponding to the same spatial locations as in (1016), (1024) repeat multiple times (1026) and calculate a difference between the second group of signals (1028). These transmit receive events (focal points) may be interleaved in time to reduce temporal artifacts. The pulse packet variation may be from altering the focus point (FIG. 17) or other characteristics of the transmit packet such as voltage (FIG. 16), aperture size, waveform, etc. The difference between the difference signals (1020, 1028) are then compared to reduce artifacts from moving blood or blood vessels, and discriminate microcalcifications (1030).

It is possible to distinguish microcalcifications based on a single transmit packet and receive event, by comparing variations between cycles in the pulse packet or between frequency components of the signal, see FIG. 2C.

Figure 3:
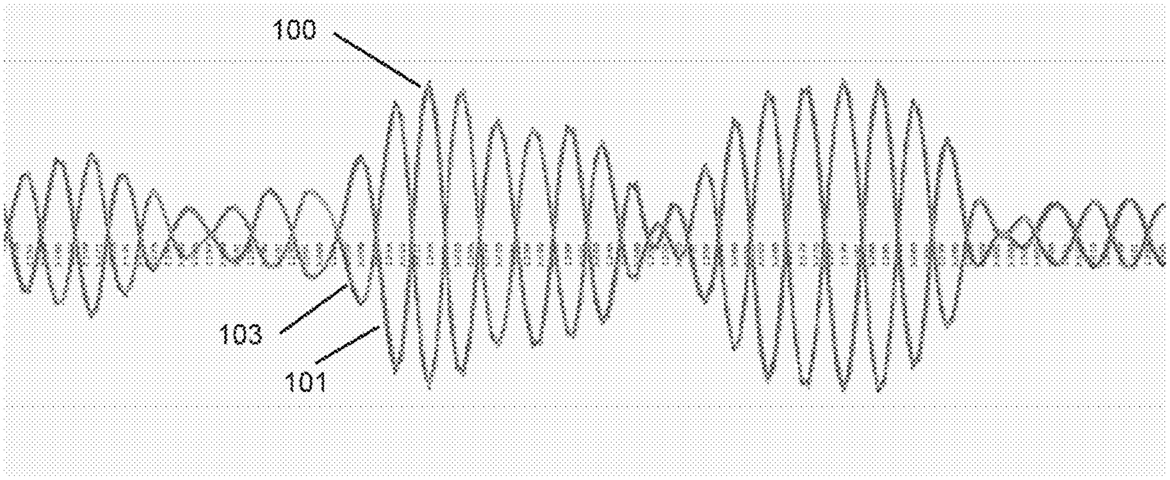
FIG. 3 illustrates an acoustic line of an agar phantom filled with corn starch to provide backscatter.

Referring to FIG. 3, an acoustic line 100 of an agar phantom filled with corn starch to provide backscatter with both 4 cycle inverted and non-inverted packets is shown. The initial pulse's acoustic line of digitizations 101 and the inverted pulse's acoustic line of digitizations 103 are shown. The agar phantom is a homogeneous medium and presents no phase aberration that would be caused in a patient by the different speeds of sound of the fat and tissues between the transducer and the reflectors, and so presents as synchronous sine waves. Phase aberration can be minimized by known ultrasonic techniques when required. The numbers on the center axis line are the individual digitations which throughout this document are made at 40 MHz or every 25 nanoseconds.

Figure 4:
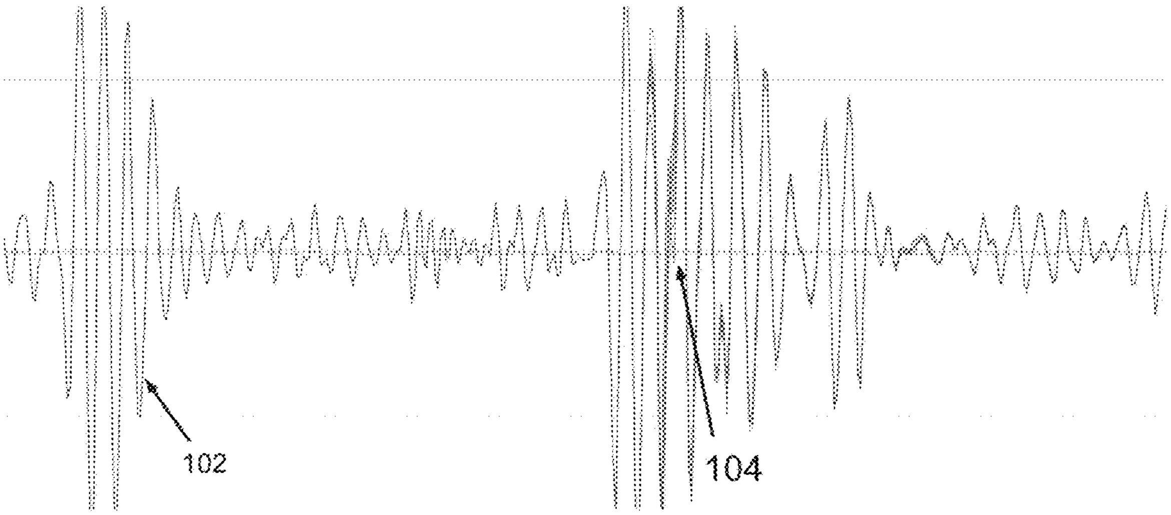
FIG. 4 illustrates an acoustic line of an agar phantom filled with corn starch to provide backscatter with a microcalcification.

FIG. 4 illustrates an acoustic line of an agar phantom filled with corn starch to provide backscatter with a microcalcification. As shown in the figure, eight acoustic lines first pass through agar with corn starch (to create backscatter) and a microcalcification of calcium Hydroxyapatite, 150-microns diameter. On the left, 102, in simulated soft tissue, the eight lines, align nearly perfectly. Towards the right, 104, the microcalcification is encountered and the lines break apart due to chaotic oscillations between the microcalcification and the background tissue.

Figure 5:
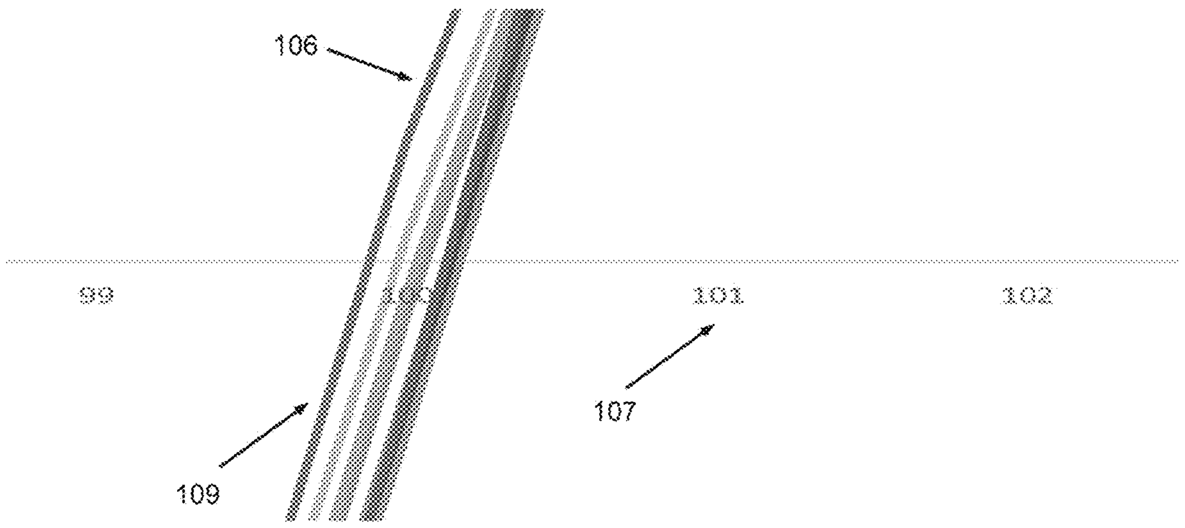
FIG. 5 illustrates a magnified view of an acoustic line at the point of the microcalcification.

FIG. 5 illustrates a magnified view of acoustic lines 106, each of a different color, at the point of the microcalcification, which is shown occurring at the 100th digitation. Reference ID number 107 indicates the digitization indicator and 109 shows the separation of the eight acoustic lines at the zero crossing point at digitization 100. From the fact that the acoustic lines 106 are spread over approximately one quarter of the digitization rate, it can be inferred that the lines separate by just less than 4-nanoseconds, which at 1540 meters per second (speed of sound in water), is implying a movement of approximately 3-microns.

Figure 6:
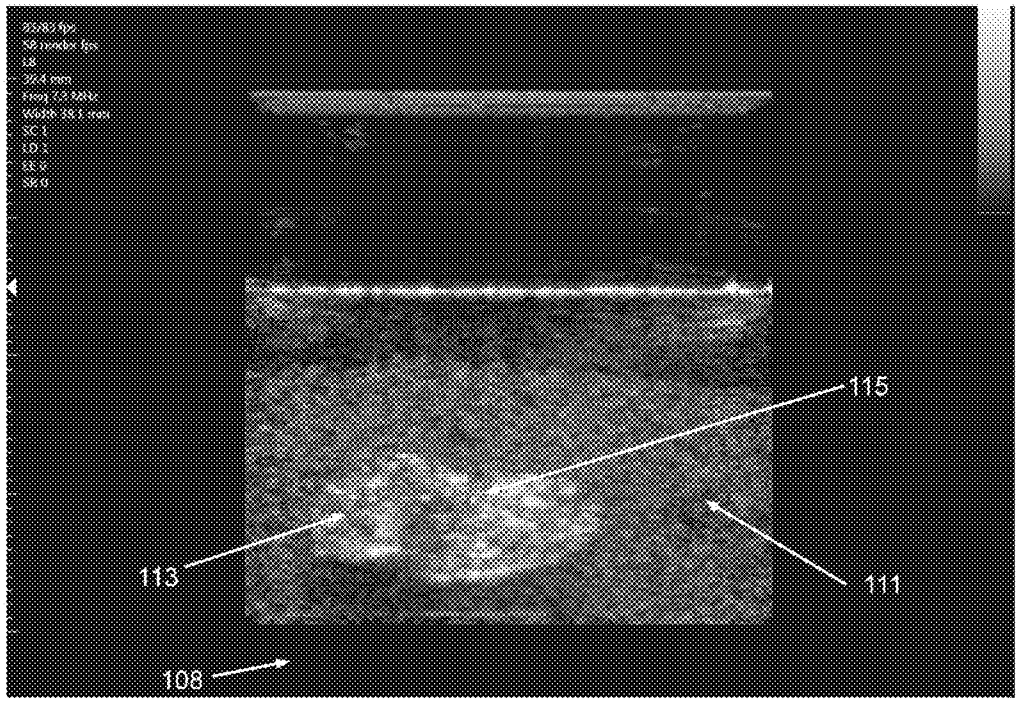
FIG. 6 illustrates a B-Mode Image fused with a CA-Mode Image of a piece of fat and muscle.

FIG. 6 shows a B-Mode Image fused with a CA-Mode Image 108 of a piece of fat 113 embedded in a gelatin phantom 111. A B-Mode Image is a greyscale image of the morphology in the lexicon of medical ultrasound. A new CA-Mode Image 115 provides the imaging of the aberrations that occur at the microcalcifications. The CA-Mode shows only the microcalcifications, but a small pinkish hint can be seen at some interfaces in the muscle. These pinkish flecks will be removed in the final CA-Mode by a threshold such as outlined in FIG. 2B.

Figure 7A:
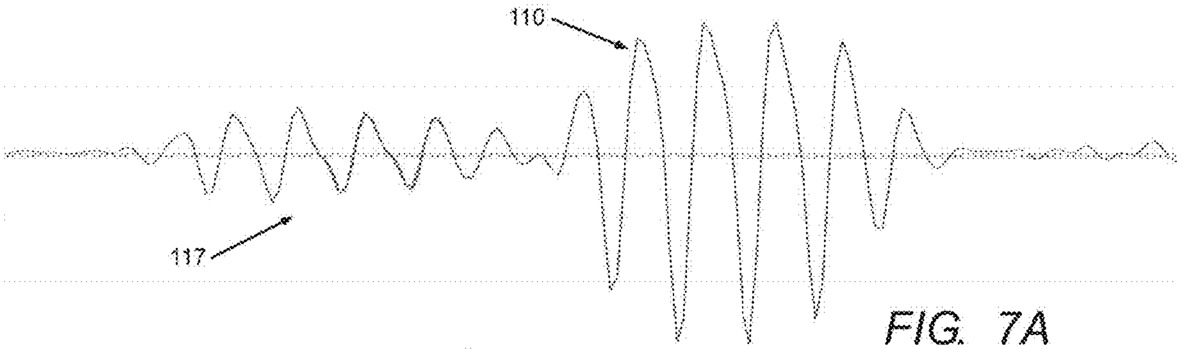
FIG. 7A illustrates digitization of an acoustic line.
Figure 7B:
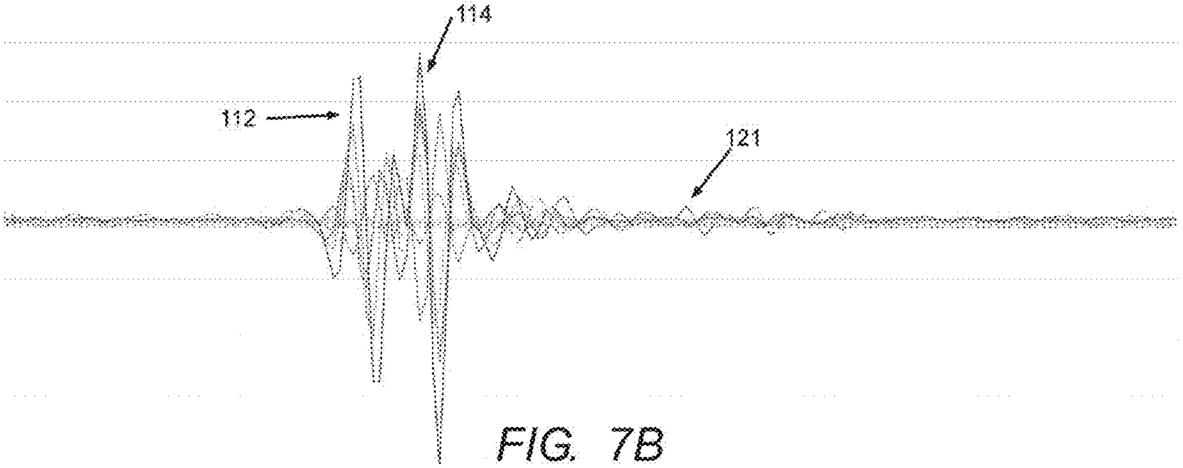
FIG. 7B illustrates subtraction of two acoustic lines separated by 200-microseconds.

FIG. 7A shows the digitization of 8 acoustic lines 110. FIG. 7B illustrates subtraction of pairs of acoustic lines. FIG. 7A shows, just visible, the breakup of the acoustic lines at the microcalcification 117. This image is the digitizations used to form one acoustic line shown in FIG. 8, which illustrates the microcalcification and boundary layer in B-Mode. FIG. 7B illustrates a graph showing the subtraction of pairs of acoustic lines 112 at the same depth. The FIG. 7B graph (subtraction) yields maximum value of 2000 at the microcalcification, and maximum value of approximately 200 at the boundary layer, which is a signal to noise value of ten, so a threshold of 250 would provide a noise free microcalcification image.

Figure 8:
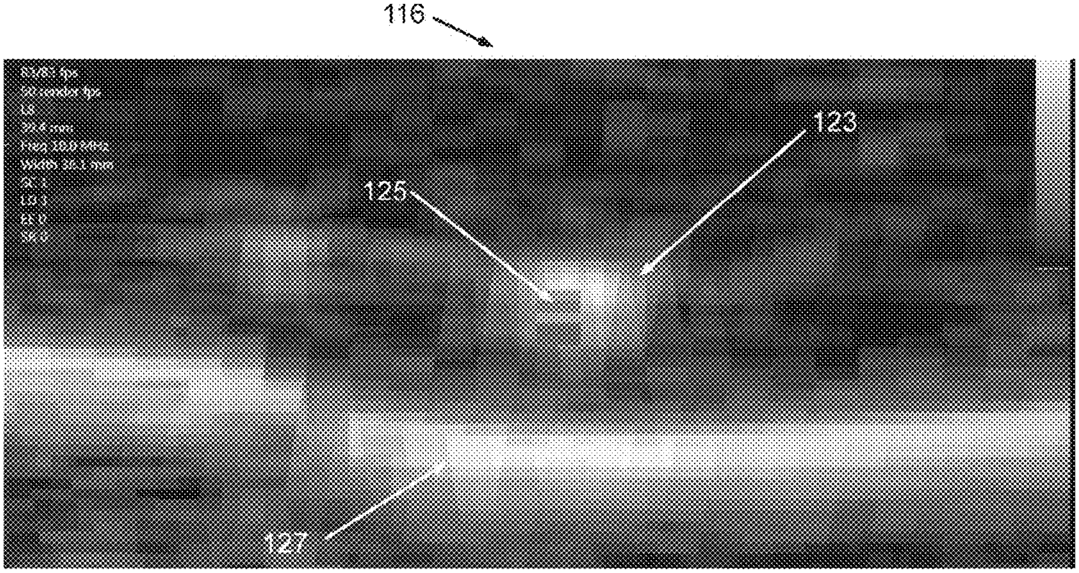
FIG. 8 illustrates a B-Mode Image fused with a CA-Mode Image of a microcalcification in front of a boundary layer.

FIG. 8 shows a magnified B-Mode Image fused with a CA-Mode Image of a microcalcification in front of a boundary layer. Note that the only place the CA-Mode shows signal is on the microcalcification.

Figure 9:
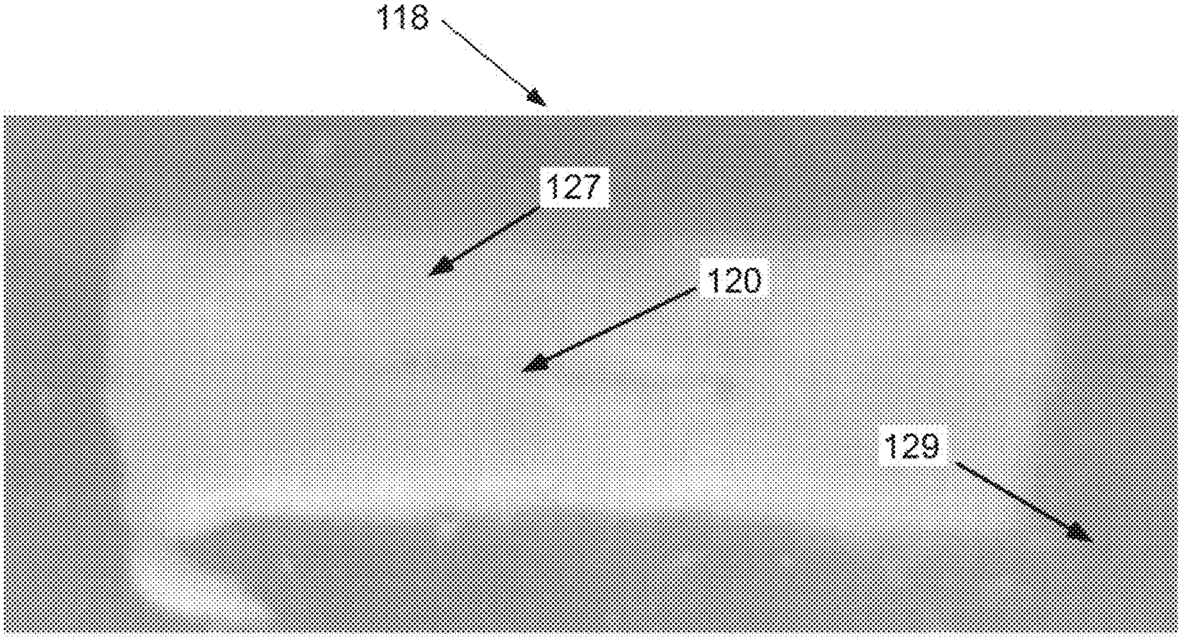
FIG. 9 illustrates a piece of pork with microcalcifications placed in a cut.

FIG. 9 illustrates a piece of pork 118 with microcalcifications placed in a cut 120 in a beaker held by gelatin. This piece of pork contains fat and muscle, and many like it have been used to create images and data.

Figure 10A:
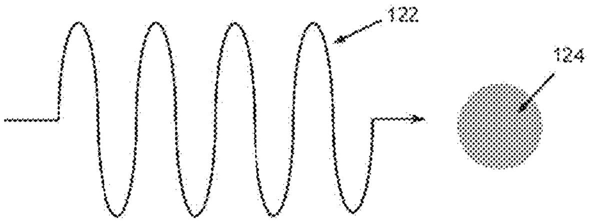
FIG. 10A illustrates one of the stages of the interaction of the transmit pulse packet and the microparticle.
Figure 10B:
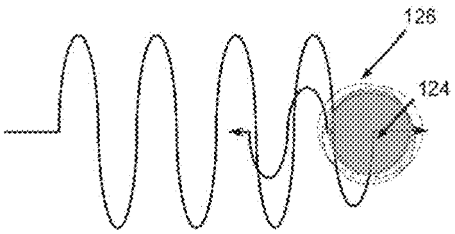
FIG. 10B illustrates one of the stages of the interaction of the transmit pulse packet and the microparticle.
Figure 10C:
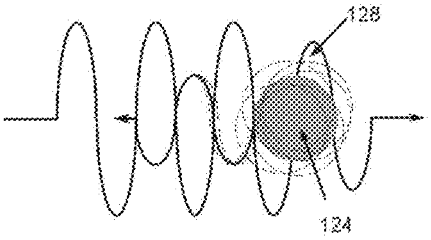
FIG. 10C illustrates one of the stages of the interaction of the transmit pulse packet and the microparticle.
Figure 10D:
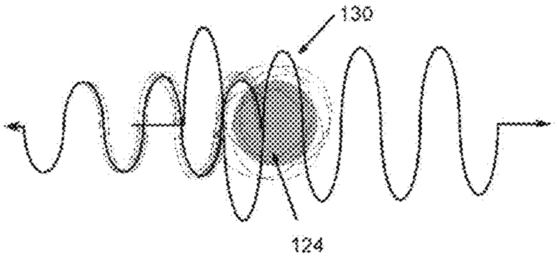
FIG. 10D illustrates one of the stages of the interaction of the transmit pulse packet and the microparticle.
Figure 10E:
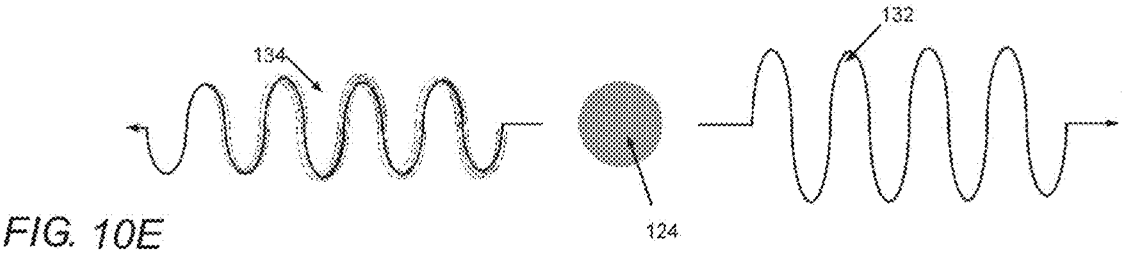
FIG. 10E illustrates one of the stages of the interaction of the transmit pulse packet and the microparticle.

FIGS. 10A-10E illustrate the stages of the interaction of the multiple super imposed transmit pulse packet events and the microcalcification. FIG. 10A shows the incoming transmit pulse packet (122) and the undisturbed (not oscillating, vibrating, or moving in random directions) microcalcification (124). FIG. 10B shows the first pulses of the incoming transmit pulse packet disturbing the microcalcification (126). FIG. 10C shows the buildup in vibration of the microcalcification and its effects on the reflected waves (128). FIG. 10D shows further escalation of the effects of more transmit pulses interacting with the microparticle and the buildup in effects on the reflected wave (130). FIG. 10E shows the reduced energy transmit wave (132) proceeding deeper into the patient and the disturbed echo pulse packet (134) returning to the transducer.

Figure 11A:
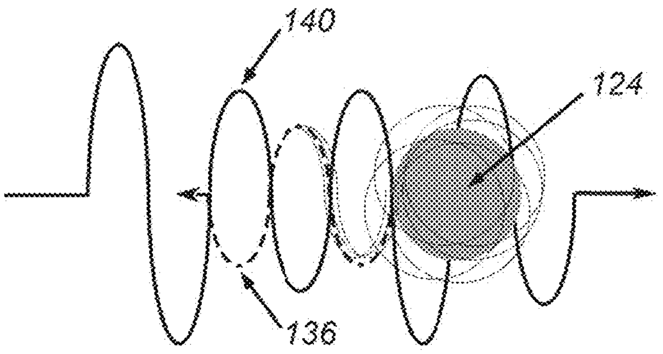
FIG. 11A illustrates the effects of the counter-propagating waves proximal to the microcalcification.
Figure 11B:
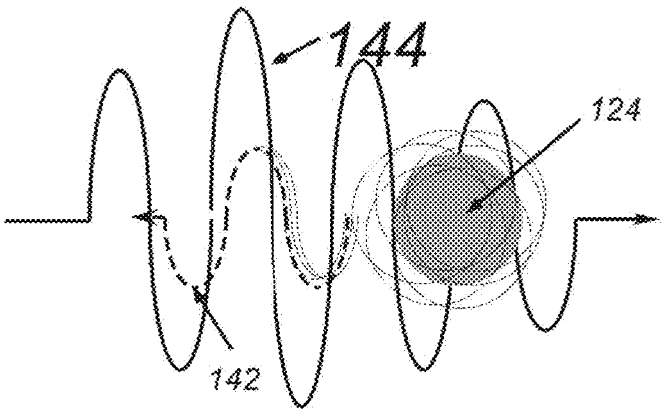
FIG. 11B illustrates the effects of the counter-propagating waves proximal to the microcalcification.

FIG. 11A and FIG. 11B show the effects of the counter-propagating waves proximal to the microcalcification at the extremes. The echo depicted as the dotted line will be launched from a plurality of positions of the microcalcification. In FIG. 11A the echo (136) is completely out of phase with the incoming Transmit Pulse Packet and will reduce the amplitude (140) of the pulse and its effects on the microcalcification. In FIG. 11B the echo (142) is more in phase with the incoming Transmit Pulse Packet and will enhance the amplitude (144) of the pulse and its effects on the microcalcification. Obviously, a microcalcification vibrating at a frequency above the pulse frequency will cause a multiple of reflections during the transit of the Transmit Pulse Packet, inducing a multitude of overlapping echoes which can be described as chaos or higher frequencies or differences in the times of flights.

Figure 12:
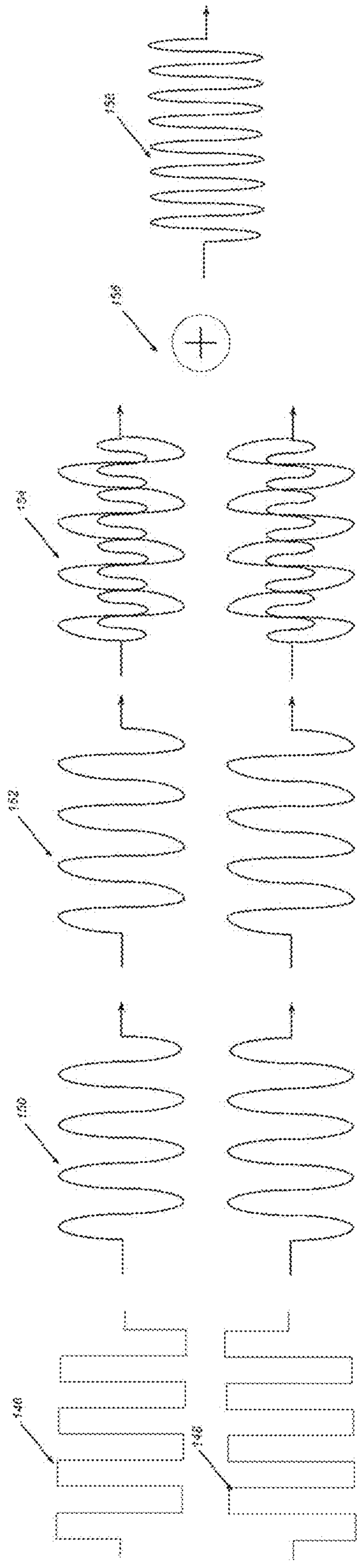
FIG. 12 is a description of the processes in pulse inversion harmonic imaging.

FIG. 12 is a description of the processes in pulse inversion harmonic imaging. The process of pulse inversion is well known in the art, and is useful for removing the fundamental transmit frequency from the signal to be analyzed. The process begins by transmitting a pulse packet (146), which the transducer, due to its limited bandwidth, will convert into approximately sine waves (150), which, after travelling through tissue which will travel faster in the compressions and slower in the rarefactions (152), will develop harmonics, (predominantly the second harmonic) (154) and the acoustic line will be recorded. The next transmit packet will be inverted from the first (148) and the same natural processes will occur. The two acoustic lines will be added (156) and the harmonic components will add together and the fundamental will cancel, leaving mostly just the even harmonic signals (158).

Figure 13A:
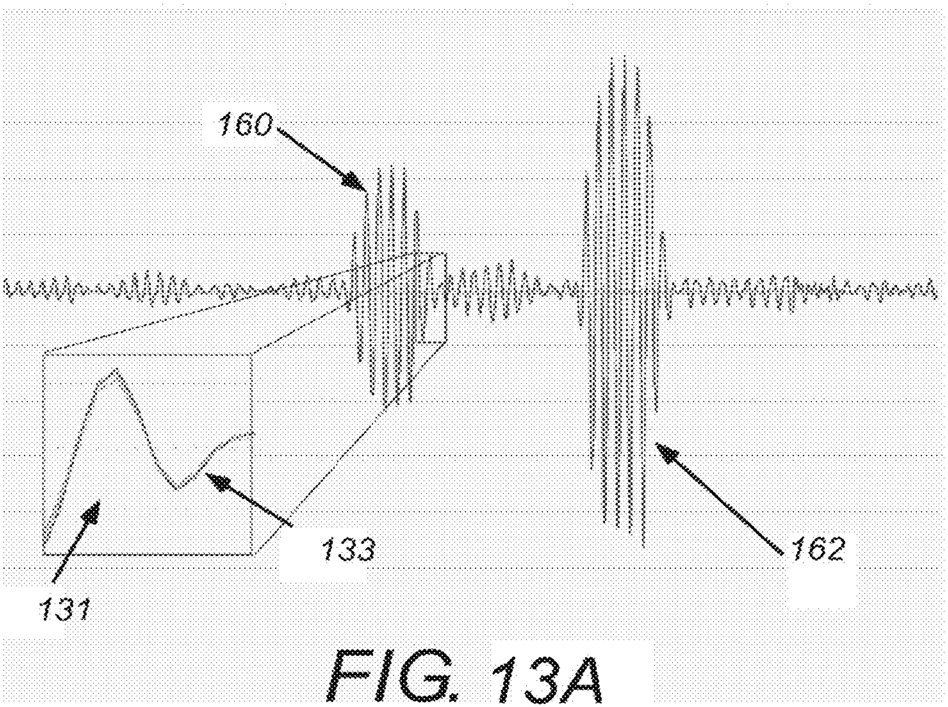
FIG. 13A illustrates different colored RF acoustic lines (eight) showing a microcalcification signal (left), followed by a boundary layer of greater acoustic reflective power (right)
Figure 13B:
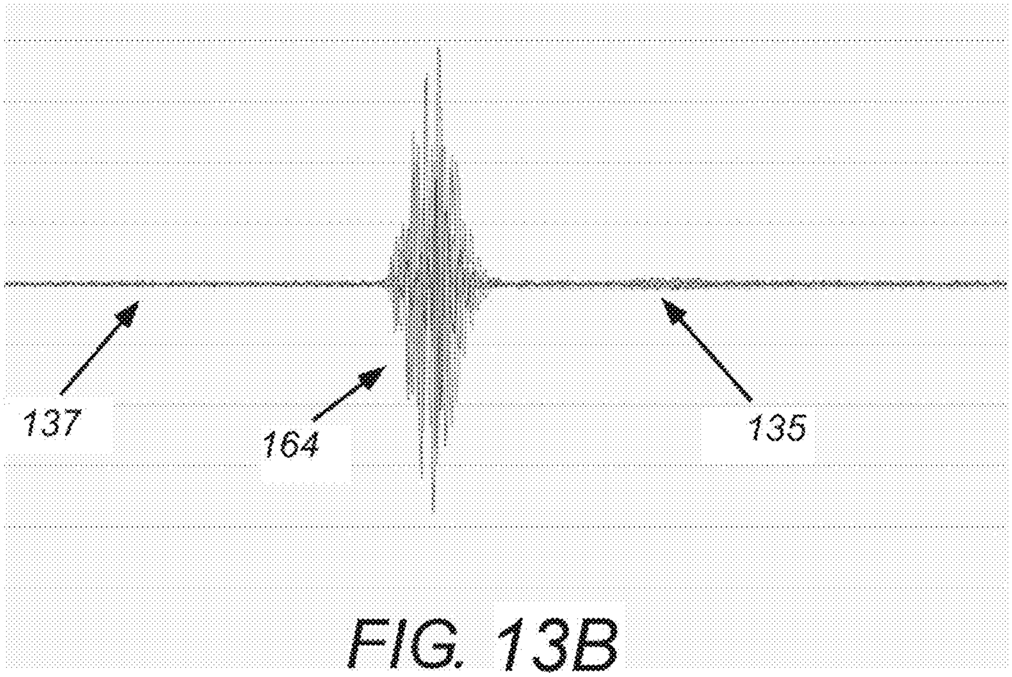
FIG. 13B illustrates the color-coded subtraction results of the eight acoustic lines (line 1-line 2, line 2-line 3, line 3-line 4 . . . line 7-line 8) shown in FIG. 11A in the same location; the magnitude of the difference between lines is significantly higher than anywhere else, even at the boundary where the echo amplitude is significantly higher.
Figure 13C:
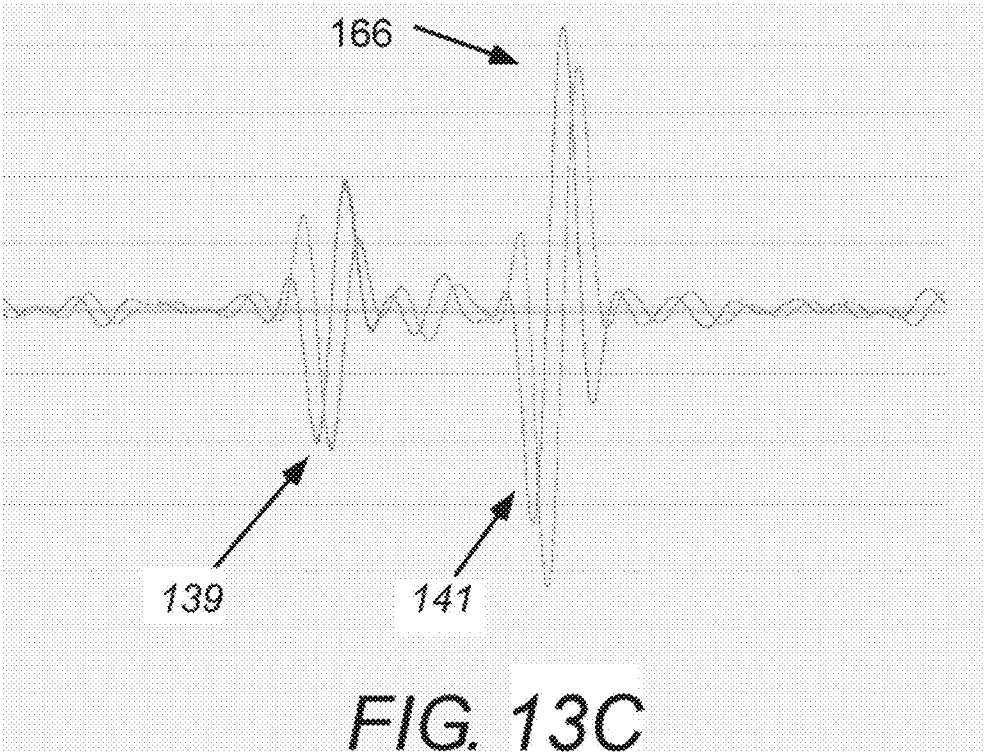
FIG. 13C illustrates an expanded section of the demodulated and filtered fundamental form for the acoustic lines gathered for FIG. 11A at the microcalcification, showing both the microcalcification and the border behind it.

FIG. 13A shows eight different RF acoustic lines showing the signal from a microcalcification on the left, 160, followed by a boundary layer of greater acoustic reflective power (right) 162. FIG. 13B illustrates color-coded subtraction results 164 of the eight acoustic lines (line 1-line 2, line 2-line 3, line 3-line 4, line 4-line 5, line 5-line 6, line 6-line 7, and line 7-line 8) shown in FIG. 13A at the same location in the acoustic lines. At the microcalcification there is a strong signal which is dependent on the power of the insonification at the microcalcification, and in this instance these results have a numerical value of 2,000 to 30,000. The subtracted lines show a very small signal at the originally larger backscatter position of the boundary layer, which in this instance typically has a numerical value of 20 to 200. FIG. 13C illustrates an expanded section of the demodulated and filtered fundamental 166 for the acoustic lines gathered for FIG. 13A at the microcalcification.

Figure 13D:
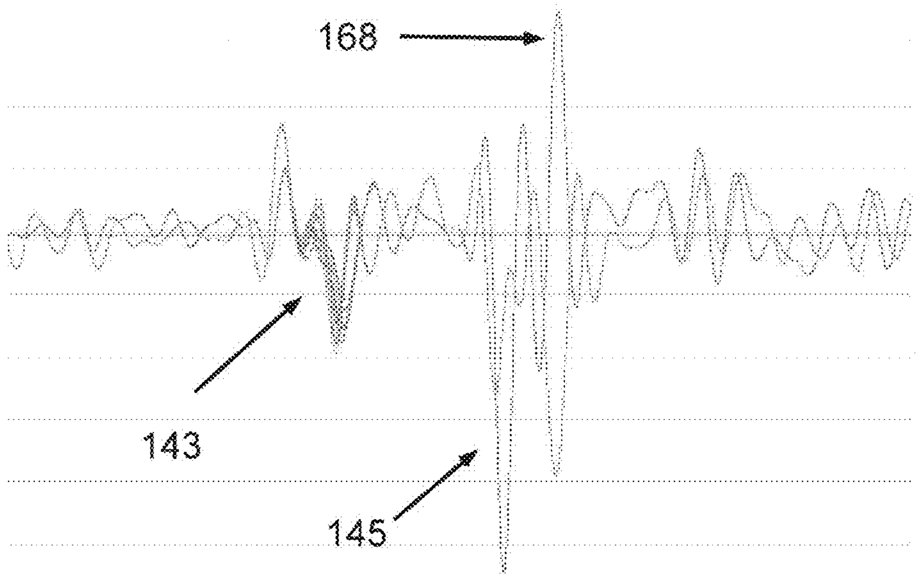
FIG. 13D illustrates the demodulated and filtered second harmonic from the acoustic lines gathered for FIG. 11A at the microcalcification, showing both the microcalcification and the border behind it.

FIG. 13C is the demodulated and filtered fundamental signals from FIG. 13A. FIG. 13D is the demodulated and filtered harmonic signal from FIG. 13A. The variations at the microcalcification in the Harmonic signal are higher than those in the fundamental, though both are present.

FIG. 13D is the demodulated and filtered second harmonic 168 from the acoustic lines gathered for FIG. 13A at the microcalcification. The ratio of the magnitudes of the fundamental to the second harmonic is found to be indicative of the spherical microcalcifications anisotropic backscatter priority of energy reflected back to the transducer.

Figure 14:
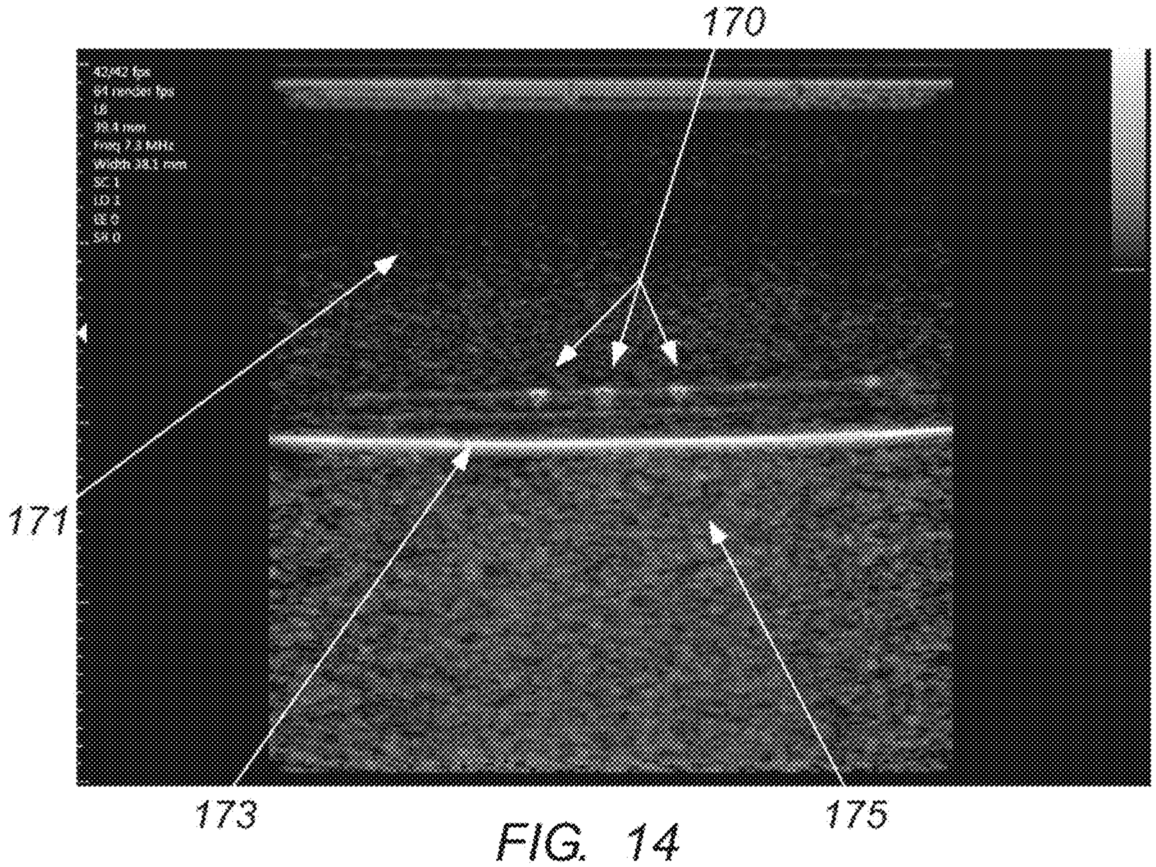
FIG. 14 illustrates an image from which the acoustic line was selected in FIGS. 11A-11D, showing the B-Mode in grayscale and the QA-Mode in red.

FIG. 14 illustrates an image from which the acoustic line was selected, FIGS. 13A, showing the B-Mode in grayscale and the CA-Mode 170 in red, which is visible only at the microcalcification in the agar phantom.

Figure 15:
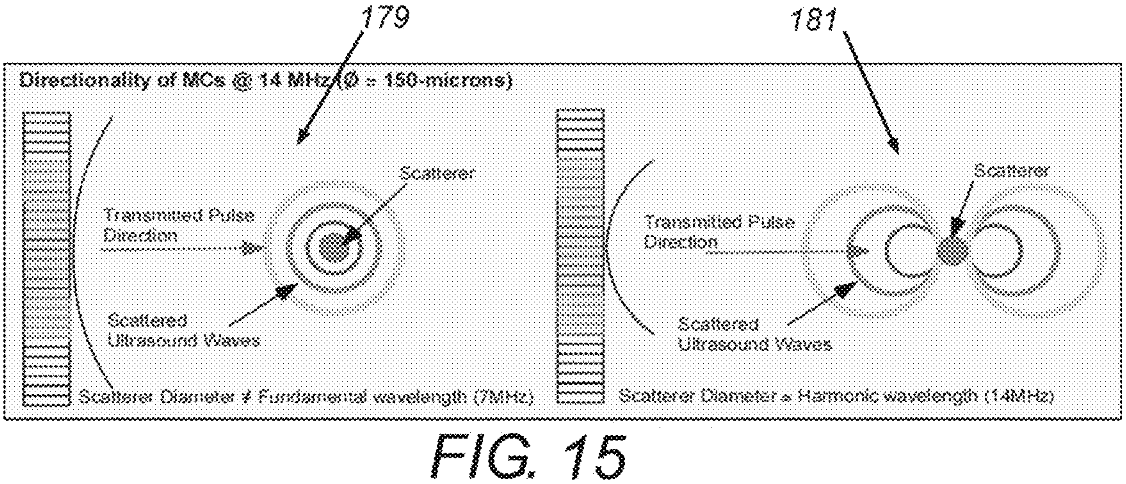
FIG. 15 is a description of the non-inotropic backscatter from a particle approximately the same size as the incident wavelength of the insonification.

FIG. 15 is a description of the non-inotropic backscatter from a particle approximately the same size as the incident wavelength of the insonification. As the fundamental has a longer wavelength than the particle size (for example, at 4 MHz the wavelength is 375 microns and the target microcalcification is 150 microns, the match is not good. The second harmonic has a wavelength of 187 microns, which is a much nearer match and the priority of the non-inotropic nature of the backscatter is clearly seen in the amplitude shown in FIG. 11C and FIG. 11D. The varying aperture made from the selection of elements shown in FIG. 13 can also be used to quantitatively assess this non-isotropic nature. The non-isotropic nature of the reflection may also be attributed to the density of the particle vs the background.

Figure 16:
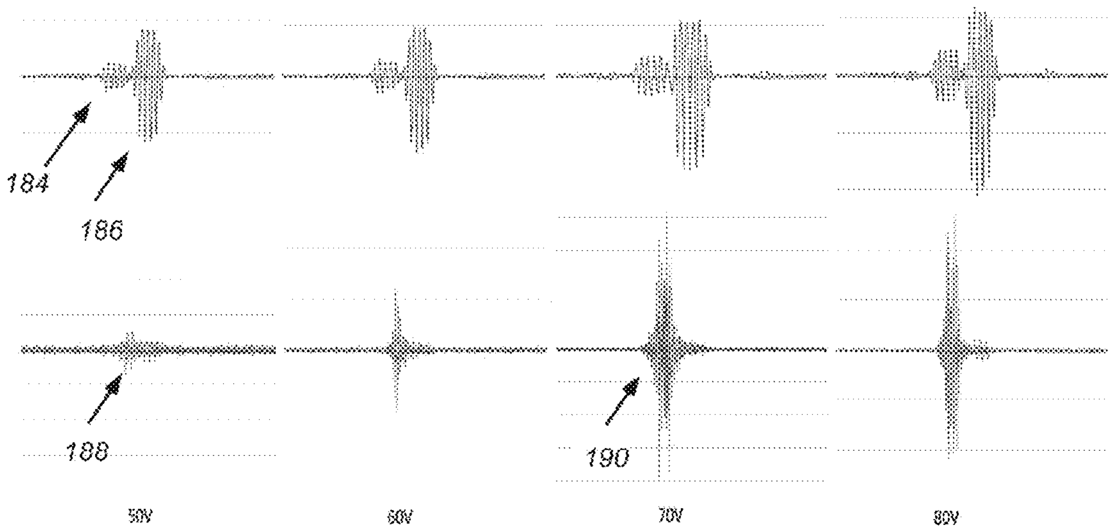
FIG. 16 illustrates the effects of increasing transmit power and its effect on chaos.

FIG. 16 illustrates four sets of eight transmit packets and received acoustic lines with the same characteristics such as phase, delay, freq, focal point, etc, but with an increasing voltage applied to the transmit packet, from 50 to 80V. The microcalcification (184) responds with significantly more chaotic oscillations with a higher transmit packet power as seen in the difference magnitude (188 vs 190) than normal tissue structures or interfaces (186).

Figure 17:
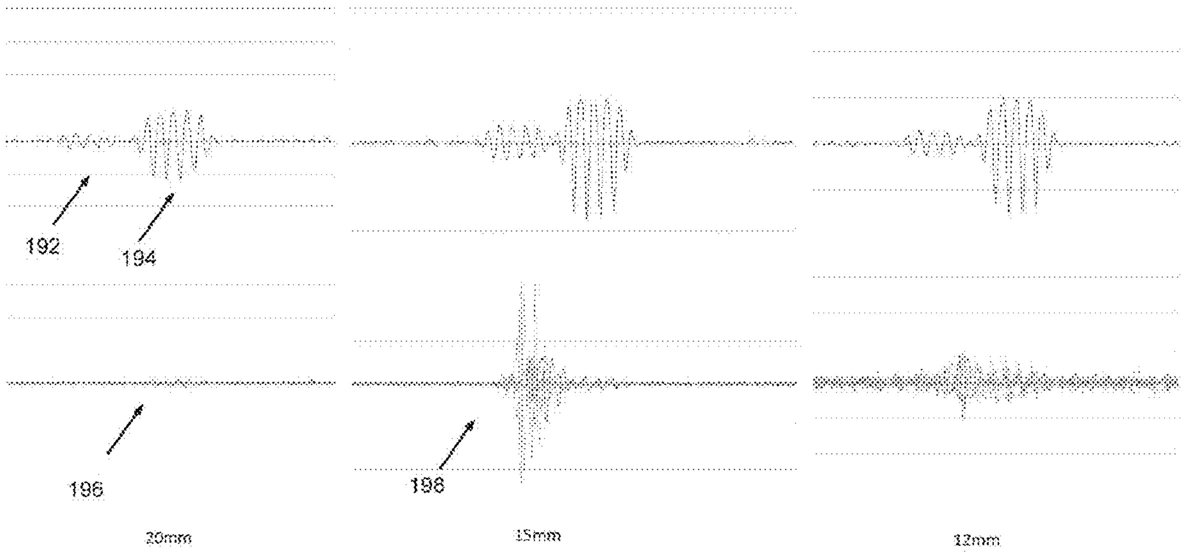
FIG. 17 illustrates the effects of changing the focal location relative to the microcalcification and its effect on the chaotic oscillations.

FIG. 17 Shows 3 sets of 8 transmit packets and received acoustic lines with the same voltage but focused at different depths (12 mm, 15 mm, 20 mm) where the microcalcification is centered at a depth of about 16 mm (192) with a defined border behind it (194). The change in the power of the transmit packet at the location of the microcalcification (192) from changing the transmit focal location shows a difference in the response of the microcalcification to the change in the amplitude of the transmit packet power at the microcalcification. Compared to the border (194) where there is little change in the difference signals (196, 198).

Once a microcalcification is detected, further investigation becomes warranted and in order to reduce processing time and computational requirements as well as directly interrogate the signal from the particle, a secondary processing component may take an FFT over the samples determined to be from the microcalcification. Faran, Bigelow, Fink, Insana, and Varghese have shown that calculating the attenuation values in the tissue field can separate out the various components of the signal. The Diffraction effects from focusing and propagation, the system transfer function, as well as the linear frequency component of attenuation in the media can be extracted in order to calculate the number of particles, the size of the particles and the impedance of the particles. Typically, this is done by building compensation matrices for the transducer being used based on data acquired from one or more well characterized phantoms. The diffraction effect and system transfer function can be extracted using either a homogenous phantom that is well characterized and or a plate in water. This allows the computation of the linear frequency component of attenuation as well as the non-linear frequency component. The non-linear frequency component holds the information relating to the size of the particles. The calculations take significant computation and therefore time, and reducing the required locations to just the microcalcifications would allow for real time discrimination of microcalcifications based on size (micro vs macro) and acoustic impedance (oxalate vs hydroxyapatite). This may also be calculated by combining parameters of the detection circuit with partial calculated attenuation parameters, such as the nonlinear response to the transmit power and or focal location, etc. whereby the curve of the response can show significant differentiation between particle sizes and impedances. This may also be combined with the bmode data, or other shorter high resolution detection capabilities for partially determining the size of the particles.

The size of the particles are typically determined by using a model to fit the shape of the reflector with the two prominent versions being a shell or spherical model. These produce bands of variation in the nonlinear frequency component of the attenuation which can be calculated based on the relative magnitude of the various frequencies of the reflected signal after compensating for imaging parameters and the attenuation properties through the propagation path.

This capability would extend beyond microcalcifications into being able to acoustically classify particles such as iron deposits or kidney stones, and beyond medical imaging into non-destructive testing for classifying defects, crystal/grain sizes, bubbles, etc. Using much longer wavelengths, the method could be adapted to seismic imaging, sonar, etc.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of using ultrasound to identify one or more particles in a region of a material having an acoustic impedance that is different than the material or background of the material, comprising:

(a) using an ultrasonic imaging system to transmit a first stimulation pulse comprising 2 to 32 cycles focused toward a spatial focal region within the region of the material and an acoustic pressure amplitude sufficient to exceed a stimulation threshold required to elicit a measurable localized displacement or oscillation of the one or more particles relative to a surrounding medium, and receive a first set of reflected signals from the stimulation pulse from a portion of the region of the material that at least partially encompasses the spatial focal region;

(b) repeating step (a) two or more additional times using the same transmit and receive conditions to obtain a first ensemble of three or more received signal sets corresponding to the spatial focal region;

(c) computing a second temporal derivative of an amplitude or phase of the received signal sets of the first ensemble across the slow time dimension at one or more spatial locations within the spatial focal region; and (d) determining a first magnitude of the second temporal derivative at each of the one or more spatial locations from the first ensemble and displaying or otherwise identifying locations of the one or more particles exhibiting an acoustic-impedance variation relative to the surrounding material;

(e) forming a second ensemble of three or more received signal sets, wherein the second ensemble is formed using one or more adjusted transmit parameters for at least a subset of the one or more spatial locations, the one or more transmit parameters comprising the spatial location of the spatial focal region and/or a change in acoustic power level, wherein, for at least the subset of the one or more spatial locations, a local acoustic power of a transmitted pulse at each spatial location in the subset is below the stimulation threshold;

(f) computing, across the second ensemble at each spatial location in the subset, a second temporal derivative of the amplitude or phase of the received signal sets of the second ensemble, and determining a second magnitude of the second temporal derivative at each spatial location in the subset; and (g) for each spatial location in the subset having data from both the first ensemble, in which the local acoustic power exceeds the stimulation threshold, and the second ensemble, in which the local acoustic power is below the stimulation threshold, comparing the magnitudes of the second temporal derivatives through slow time as determined in accordance with step (d) and step (f), to identify the one more particles exhibiting the acoustic-impedance variation by determining that the magnitude present in the first ensemble diminishes or disappears in the second ensemble, and rejecting signals that persist in the second ensemble as not caused by the stimulation pulse.

2. The method according to claim 1, wherein said one or more particles is a microcalcification.

3. The method according to claim 1, wherein said material is a mammalian tissue.

4. The method according to claim 1, wherein said material is a mammalian organ.

5. The method according to claim 3, wherein said mammalian tissue is a human tissue.

6. The method according to claim 4, wherein said mammalian organ is a human organ.

* * * * *